(12) United States Patent
Sama et al.

(10) Patent No.: US 12,088,125 B2
(45) Date of Patent: Sep. 10, 2024

(54) DEVICES AND METHODS FOR FINE-TUNING ALIGNMENT OF CHARGING DEVICE WITH IMPLANTED MEDICAL DEVICE

(71) Applicant: Axonics, Inc., Irvine, CA (US)

(72) Inventors: Rinda Sama, Irvine, CA (US); Faizal Abdeen, Mission Viejo, CA (US)

(73) Assignee: Axonics, Inc., Irvine, CA (US)

( * ) Notice: Subject to any disclaimer, the term of this patent is extended or adjusted under 35 U.S.C. 154(b) by 541 days.

(21) Appl. No.: 17/522,644

(22) Filed: Nov. 9, 2021

(65) Prior Publication Data

US 2022/0149671 A1    May 12, 2022

Related U.S. Application Data

(60) Provisional application No. 63/111,491, filed on Nov. 9, 2020.

(51) Int. Cl.
| | |
|---|---|
| *H02J 50/90* | (2016.01) |
| *A61N 1/372* | (2006.01) |
| *A61N 1/378* | (2006.01) |
| *H02J 7/00* | (2006.01) |
| *H02J 50/10* | (2016.01) |
| *H02J 50/80* | (2016.01) |

(52) U.S. Cl.
CPC .......... *H02J 50/90* (2016.02); *A61N 1/37223* (2013.01); *A61N 1/37247* (2013.01); *A61N 1/3787* (2013.01); *H02J 7/0047* (2013.01); *H02J 50/10* (2016.02); *H02J 50/80* (2016.02)

(58) Field of Classification Search
CPC ....................................................... H02J 50/90
USPC ............................................................ 320/108
See application file for complete search history.

(56) References Cited

U.S. PATENT DOCUMENTS

| | | | |
|---|---|---|---|
| 2005/0038332 A1* | 2/2005 | Saidara | G16H 40/67 128/920 |
| 2017/0143981 A1* | 5/2017 | Aghassian | A61N 1/3787 |
| 2017/0155194 A1* | 6/2017 | Kanno | G06K 7/10 |
| 2019/0148968 A1* | 5/2019 | Kim | H04B 5/79 320/108 |

* cited by examiner

*Primary Examiner* — Yalkew Fantu
(74) *Attorney, Agent, or Firm* — Gordon Rees Scully & Mansukhani, LLP

(57) ABSTRACT

Devices, systems and methods for improved alignment of a charging device for an implanted medical device are disclosed herein. The system can include a charging device that outputs one or more charge parameters during charging to an external user device that outputs an alignment indicator to facilitate fine-tuned alignment of the external charging device. The indicator can be a dynamically updated while adjusting alignment of the charging device. The indicator can includes any of a visual, audio, or haptic output. The user device can be a clinician programmer, patient remote, or a patient's personal computing device. The functionality of the indicator can be incorporated into the charging device itself or distributed across multiple devices to allow fine-tuning of alignment remotely. The alignment feature can be included in a device of a clinical specialist or field technician for troubleshooting alignment problems experienced by some patients.

23 Claims, 22 Drawing Sheets

DEVICES AND METHODS FOR FINE-TUNING ALIGNMENT OF CHARGING DEVICE WITH IMPLANTED MEDICAL DEVICE

CROSS-REFERENCES TO RELATED APPLICATIONS

This application is a Non-Provisional of and claims the benefit of priority of U.S. Provisional Application No. 63/111,491 filed Nov. 9, 2020, the entirety of which is incorporated by reference herein.

FIELD

The present invention relates to implantable neurostimulation treatment systems and associated charging devices and methods.

BACKGROUND

The prevalence of use of medical devices in treating ailments is increasing with time. In many instances, and as these medical devices are made smaller, these medical devices are frequently implanted within a patient. To power such devices, external charging devices that transcutaneously transfer energy to the implanted device are used to power the implanted device or to recharge an rechargeable battery of the implanted device. Such external charging devices typically utilize an charging coil that inductively couples with an internal coil of the implanted medical device. Efficient transcutaneous transfer of energy requires that the coils be suitably aligned. Misalignment can result in failure to recharge, inefficient recharging and/or excessive heat generation. While some conventional systems include features to indicate alignment, these features typically indicate merely when alignment is suitable for charging to take place within acceptable limits and typically do not facilitate precision placement to ensure optimal charging occurs. This can result in sub-optimal alignment that leads to prolonged recharging times and/or excessive heat generation. Further, current approaches of indicating alignment typically lack detailed guidance to facilitate the patient or clinician in providing precision alignment.

Therefore, there exists a need for devices, systems and methods that facilitate improved, precision alignment between an external charging device and an implanted medical device. There is further need for an approach that provides guidance on improving alignment in a manner that is intuitive, interactive and utilizes features of existing systems.

BRIEF SUMMARY

In one aspect, the invention pertains to charging of an implantable pulse generator by an external charging device, and particularly, devices and methods for improving alignment between charging coils of an implanted medical device and external charging device.

In some embodiments, the system is configured such that a device determines an alignment indicator based on charging efficiency determined from charging parameters. The system outputs the indicator, which corresponds to alignment, during charging. Typically, the indicator indicates alignment without modifying the charging operation based on the alignment determination. This indicator facilitates fine-tuned precision adjustment of alignment, either by the patient or clinician, during the charging operation. In one aspect, the alignment feature described herein can be incorporated into a user device of a clinical specialist (e.g. field technician associated with the device manufacturer) to allow the specialist to assist the physician and/or patient in positioning the device. Such a feature is particularly advantageous for troubleshooting alignment problems experienced by some patients. In some embodiments, the alignment feature can be embodied in a software application accessible/authorized for use only by the clinician specialist, not by a physician or clinician device. These aspects can be applied to any of the embodiments described herein.

In some embodiments, the system includes a first indicator that indicates a first-order alignment (rough alignment) that corresponds to when alignment between coils is sufficient to inductively transfer energy for transcutaneously charging, and a second indicator that indicates a second-order alignment (precision alignment) within a range of suitable alignment positions to facilitate fine-tuned adjustment of alignment to increase charging efficiency and reduce charging time. In some embodiments, the system can include a third indicator that indicates when the optimal alignment position is reached. The first, second and third indicators are distinct from each other so that a user and/or clinician can readily distinguish between each indicator. In some embodiments, the charging device includes certain indicators for indicating a first order alignment (i.e. rough alignment) so that the user can determine whether initial placement is suitable to establish inductive coupling and commence charging, and certain other alignment indicators are used to indicate a second order alignment (e.g. fine-tined alignment during charging to improve or optimize charging). Typically, loss of first order alignment loses inductive coupling, which stops charging completely, whereas losing second order alignment reduces charging efficiency/optimization during charging. In some embodiments, the certain other alignment indicators are indicators provided by the charging device that are readily distinguishable from the first order indicators. In some embodiments, the certain other alignment indicators are provided by an external user device (e.g. smartphone, tablet) of the patient or clinician. The certain other alignment indicators can be determined and output by a specialized software application on a standard user device specific for improving alignment of the charging device. In some embodiments, the certain other indicators for second-order alignment are only provided by the user device. In some embodiments, the charging device includes the first-order alignment indicators, while the user device includes indicators for both first-order alignment and second-order alignment.

In some embodiments, the alignment indicator is determined during standard charging operation and output to a user and/or clinician in real-time during charging to allow the user and/or clinician to dynamically adjust the alignment of the charging device based on the indicator. The indicator can be incorporated into the charging device, or can be provided by a user interface of one or more external devices. The indicator can include any of or any combination of: visual, audio, and haptics. In some embodiments, the indicator can be provided on or across multiple devices, for example, the indicator can be provided on both a clinician and patient device, for example, a first indicator can be provided by the charging device and the second and/or third indicator can be provided on one or more external computing devices of the patient or clinician. This allows additional functionality in regard to precision placement to complement existing charging devices already having minimal alignment features.

In some embodiments, the external charging device includes a power button and one or more visual indicators, such as one or more light indicators (e.g. flashing, on, off) and one or more audio indicators (e.g. one or more tones/beeps). The light indicators can be used to indicate any of: a power state (e.g. green on), a battery state of the external device (e.g. orange, orange flashing), error states (e.g. red), and charging status (e.g. flashing green). In some embodiments, the charging device charges the implanted medical device in a closed-loop charging state during standard charging and an open-loop loop charging state if the implanted medical device battery is too low to perform closed loop charging and can optionally include various other charging states (e.g. slow charge, fast charge, etc.) In some embodiments, any indicator of the charging device that indicates charging does not identify or distinguish between the differing charge states. The audio indicators can be used to indicate any of: initial alignment suitable that commences charging (e.g. long tone), completion of charging (e.g. three rising tones) and error states. In some embodiments, the external charging device includes a haptic indicator for indicating a change in charge status necessitating user intervention (e.g. first order misalignment, loss of charge coupling). This is particularly advantageous when the implanted medical device is implanted in the lower back/upper buttock region where the patient cannot view visual indicators on the charging device. This implantation region is common in sacral neuromodulation systems for treatment of urinary and/or fecal incontinence. The use of a haptic feature for loss of alignment/charging facilitates an immediate patient response to correct/re-align the charging device to restore charging. Notably, conventional device typically rely on assortment of audio and visual indicators (e.g., various patterns of beeps and flashing lights), which can be more easily disregarded or confused by the patient, which may cause undue delay in restoring charging. When first order alignment is unsuitable, charging stops completely, such that the implanted medical device may not be able to be charged within the time available to the patient or greatly prolonging the charging session, therefore, it is advantageous for this event to be indicated by a unique indicator (e.g. haptic vibration) that is instantly recognizable by the patient and easily distinguished from the assorted beeps/flashing lights commonly used for various other charging events (e.g. starting, charging status, battery, completion, etc.). In some embodiments, the charging device includes a haptic indicator only for loss of charging due to misalignment in first-order alignment.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1:
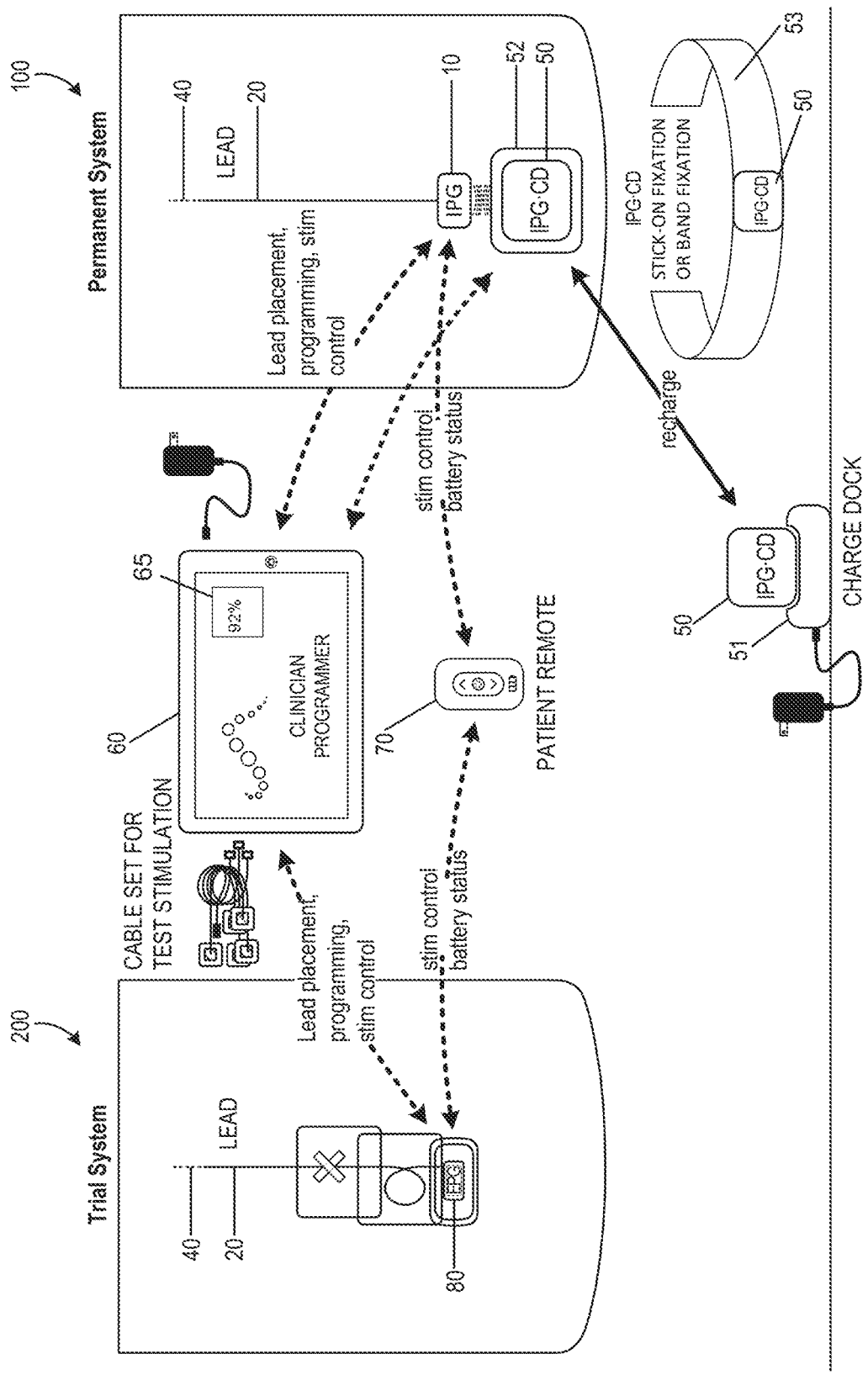
FIG. 1 schematically illustrates a nerve stimulation system, which includes a clinician programmer of both a trial neurostimulation system and a permanently implanted neurostimulation system, in accordance with some embodiments of the invention.

The present invention relates to recharging of implanted medical devices, in particular, neurostimulation treatment systems and associated devices. In some embodiments, the invention relates to charging of an implanted neurostimulator of a sacral nerve stimulation treatment systems configured to treat overactive bladder ("OAB") and relieve symptoms of bladder related dysfunction. It will be appreciated, however, that the present invention may also be utilized for any variety of neuromodulation uses, such as fecal dysfunction, the treatment of pain or other indications, such as movement or affective disorders, as well as various other implantable medical devices as understood by one of skill in the art.

In some embodiments, the invention pertains to a device that obtains one or more charging parameters from the charging device and/or the implantable neurostimulator and outputs an alignment indicator based on the one or more charging parameters that is indicative of precision alignment between the charging device and implanted device. Currently, many implantable neurostimulation system include a receiving coil that receives energy transcutaneously from a charging coil in an external charging device placed on the patient's skin over the charging device. Exemplary charging device are described in U.S. application Ser. No. 16/816,006, and U.S. Pat. No. 10,682,521, the entireties of which are incorporated herein by reference or all purposes. The precise alignment between the charging coil and the receiving alignment, including alignment along x and y axes along the patients skin, as well as rotational orientation, largely determines the efficiency of charging. Typically, conventional systems provide charging so long as the charging device is within the range of suitable positions, however, many positions within this range may provide suboptimal charging at reduced charging efficiency, which can lead to patient discomfort and poor charging, as described above. Thus, the invention allows for precision placement of the charging device to fine-tune alignment between the coils of the charging device and the implanted neurostimulator. It is appreciated that although the concepts herein are described in regard to a particular type of neurostimulation system, the concepts described herein are applicable to any type of neurostimulation system and further applicable to any charging device for an implanted medical device that would benefit from optimal alignment and placement on the patient.

I. Neurostimulation Indications

Neurostimulation (or neuromodulation as may be used interchangeably hereunder) treatment systems, such as any of those described herein, can be used to treat a variety of ailments and associated symptoms, such as acute pain disorders, movement disorders, affective disorders, as well as bladder related dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency—frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 33 million Americans suffer from OAB. Of the adult population, about 30% of all men and 40% of all women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG), also referred to herein as an "implantable neurostimulator" or a "neurostimulator." The safety and effectiveness of SNM for the treatment of OAB, including durability at five years for both urge incontinence and urgency-frequency patients, are supported by multiple studies and are well-documented. SNM has also been approved to treat chronic fecal incontinence in patients who have failed or are not candidates for more conservative treatments.

A. Implantation of Sacral Neuromodulation System

Currently, SNM qualification has a trial phase with an external neurostimulator, and is followed if successful by a permanent implant with a fully implantable, rechargeable neurostimulator. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients. The present invention relates to a system adapted to deliver neurostimulation to targeted nerve tissues in a manner that disrupts, inhibits, or prevents neural activity in the targeted nerve tissues so as to provide therapeutic effect in treatment of OAB or bladder related dysfunction. In one aspect, the system is adapted to provide therapeutic effect by neurostimulation without inducing motor control of the muscles associated with OAB or bladder related dysfunction by the delivered neurostimulation. In another aspect, the system is adapted to provide such therapeutic effect by delivery of sub-threshold neurostimulation below a threshold that induces paresthesia and/or neuromuscular response or to allow adjustment of neurostimulation to delivery therapy at sub-threshold levels.

Figure 3:
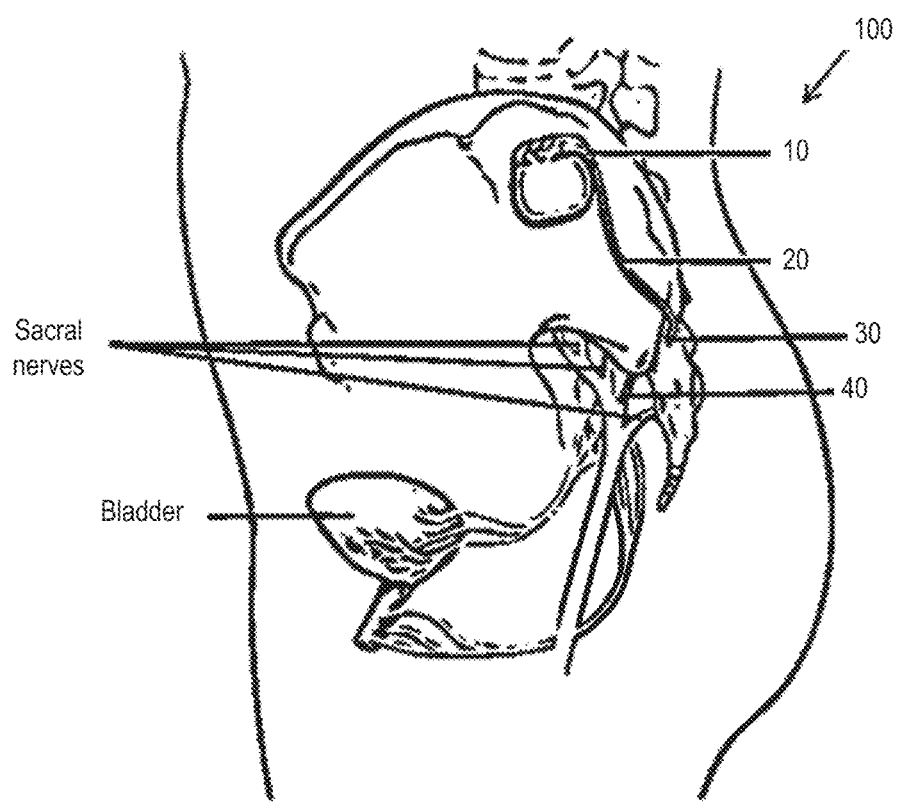
FIG. 3 shows an example of a fully implanted neurostimulation system, in accordance with some embodiments.

Sacral nerve modulation applications typically involve implantation of the implantable neurostimulation device in the lower back/upper buttock region of the patient to better access the sacral nerve through the sacrum (see FIG. 3). This placement of the external charging device can be difficult to observe for the patient, thereby frustrating precision placement, particularly over time due to migration and fluctuations in body weight. While current neurostimulation systems have provided marked improvements in efficiency of stimulation, such systems typically require periodic recharging by use of an external charging device positioned on the patient over the device. Typically, the patient recharges the neurostimulator on a periodic basis, such as every few days, weekly or monthly, depending on the frequency of use and stimulation level of therapy. If the charging device is optimally placed, many implantable neurostimulators can be recharged in less than two hours, often within an hour or less, with minimal patient discomfort. However, if not precisely placed, recharging can take notably longer, for example, well over an hour, such as three or more hours. Further, suboptimal placement can result in build-up of excessive heat and the prolonged contact of the external charging device can cause considerable annoyance and patient discomfort. Therefore, it is desirable to provide devices and methods that facilitate precision placement of the charging device with accuracy and consistency, as described further below.

B. Example Embodiments

FIG. 1 schematically illustrates an exemplary nerve stimulation system, which includes both a trial neurostimulation system 200 and a permanently implanted neurostimulation system 100, in accordance with aspects of the invention. The EPG 80 and IPG 10 are each compatible with and wirelessly communicate with a clinician programmer 60 and a patient remote 70, which are used in positioning and/or programming the trial neurostimulation system 200 and/or permanently implanted system 100 after a successful trial. As discussed above, the clinician programmer can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

To further improve placement of the charging device on the patient to provide optimal, fine-tuned alignment, the system can include an alignment indicator on a user device or the charging device itself that allows the user to observe a real-time indicator of coil alignment during manual positioning of the charging device. This feature is particularly applicable to a sacral neurostimulation system, such as that described, since the implantable pulse generator is implanted in the patient's lower back/upper buttock region, where it can be difficult for the patient to view placement during manual positioning of the charging device. In the embodiment in FIG. 1, the clinician programmer 60 includes alignment indicator 65 that is configured to display an alignment indicator, which can be used by the clinician to facilitate precise placement of the charging device by viewing one or more charging parameters or associated charging metric in real-time during the charging operation.

In another aspect, the implantable permanent system includes a charging device 50 that is configured to transcutaneously charge the implantable pulse generator by inductively coupled coils. Typically, the implantable pulse generator includes a single receiving coil and the charging device 50 includes a single transmitting coil. When the charging device 50 is placed in proximity to the implantable pulse generator, the charging device and implantable pulse generator establish communication and initiate a charging protocol. Upon initiation of an alignment procedure upon receiving a request by the external device, the charging device 50 can output one or more charging parameters, and or utilize an alignment module that is distinct from a charging module to determine and output the charging parameters or an alignment metric to the external device. The charging device 50 can also include an adhesive attachment device 52 or charging belt 53 to maintain the charging device 50 in position on the patient during charging.

The clinician programmer 60 has a control unit which can include a microprocessor and specialized computer-code instructions for implementing methods and systems for use by a physician in deploying the treatment system and setting up treatment parameters. The clinician programmer generally includes a user interface which can be a graphical user interface and can further include audio and haptic features as well. The clinician programmer 60 can be configured with specialized software applications, for example, specialized alignment software that determines and output an alignment indicator to guide a user through a fine-tuned charging device alignment procedure. As noted above, the clinician programmer can include a module with hardware and computer-code to execute analysis of charging parameters for determining charging efficiency, where the module can be a component of the control unit microprocessor, a pre-processing unit coupled to or in-line with the stimulation and/or sensory cables, or the like.

In this embodiment, the clinician program 60 communicates directly with the charging device 50 and obtains one or more charging parameters during charging. The clinician programmer 60 provides the alignment indicator 65, which can be a dynamically updated display of the charging parameters or associated metric (e.g. charging efficiency) to enable the clinician to observe the strength of efficiency of charging during manual adjustment of the position of the charging device 50. In one aspect, the charging device is communicatively coupled to the clinician programmer 60 by shortwave radio communication (e.g. Bluetooth), while currently communicating to the implantable pulse generator through another communication scheme (e.g. MedRadio). In some embodiments, the clinician programmer 60 obtains the one or more charging parameters from the charging device 50 but does not otherwise modify the charging operation based on alignment determinations. In some embodiments, the alignment indicator 65 can further provide a spatial illustration of the position of the charging device relative the implantable medical device. In other embodiments, the clinician programmers can utilize various other means of indicating alignment, including but not limited to: haptic, visual (e.g., LED, graphic), or audio (e.g. beep or alert) to indicate optimization of alignment. In some embodiments, the indicator can include multiple different types of notifications or a notification that changes as the charging device is adjusted and nears optimal placement. It is appreciated that the alignment indicator, including any of the features noted above, can be incorporated into the charging device itself, or can be provided on another user device, for example a device of the patient, such as the patient remote or a personal computing device (e.g. smartphone, tablet).

Figure 2A:
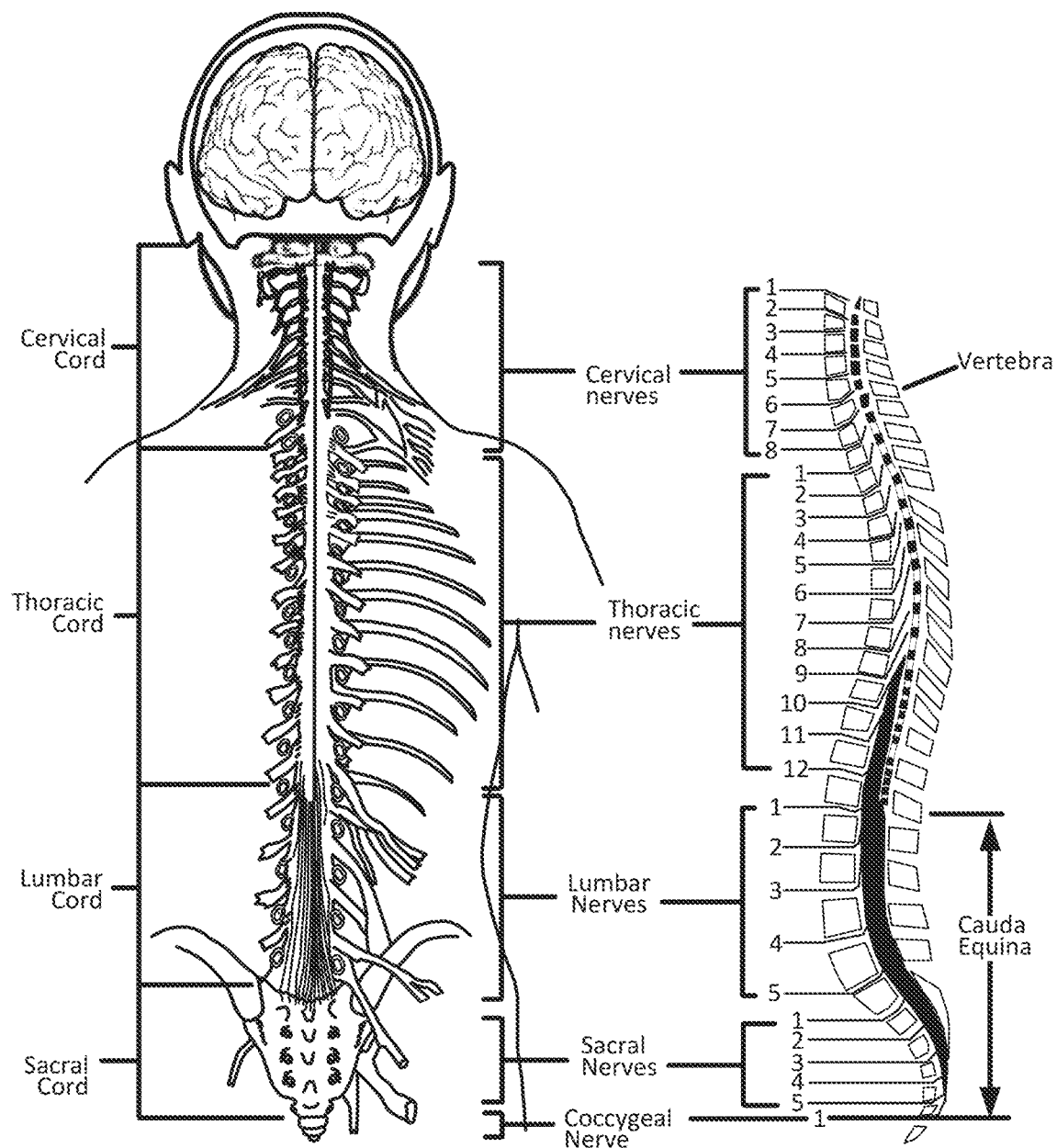
FIGS. 2A-2C show diagrams of the nerve structures along the spine, the lower back and sacrum region, which may be stimulated in accordance with some embodiments.
Figure 2B:
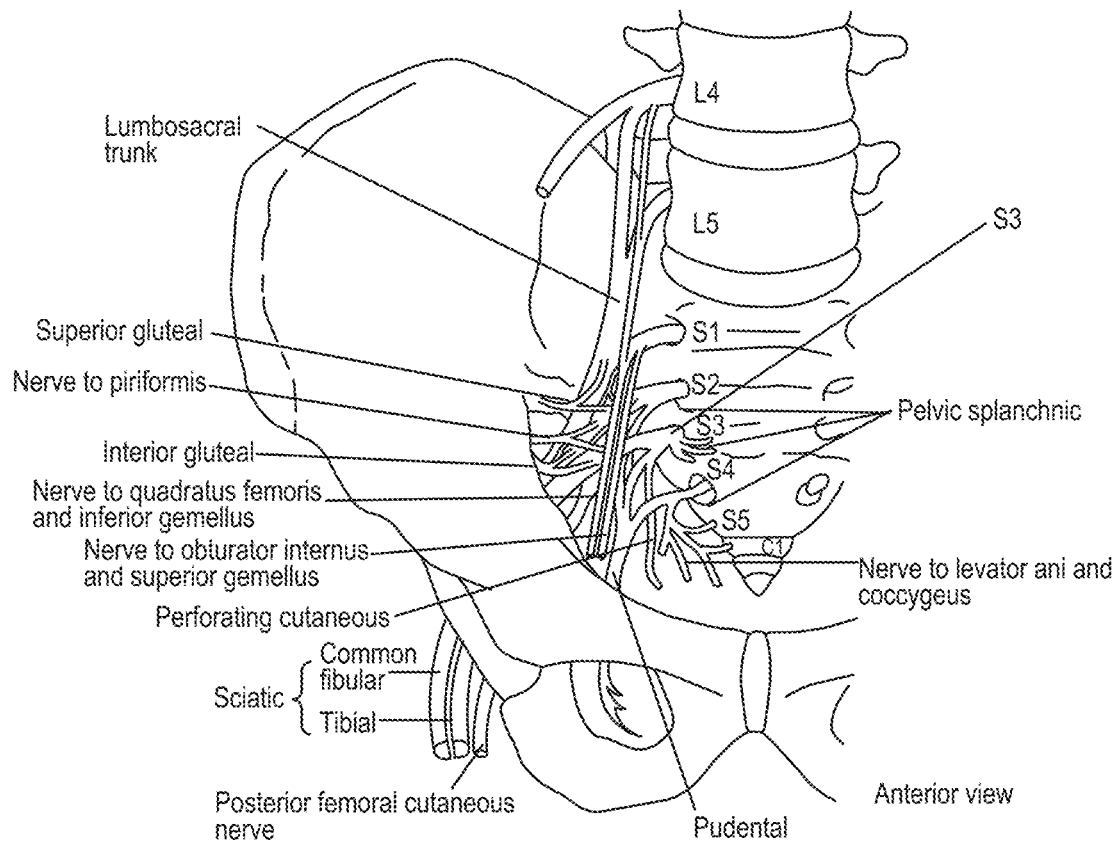
Figure 2C:
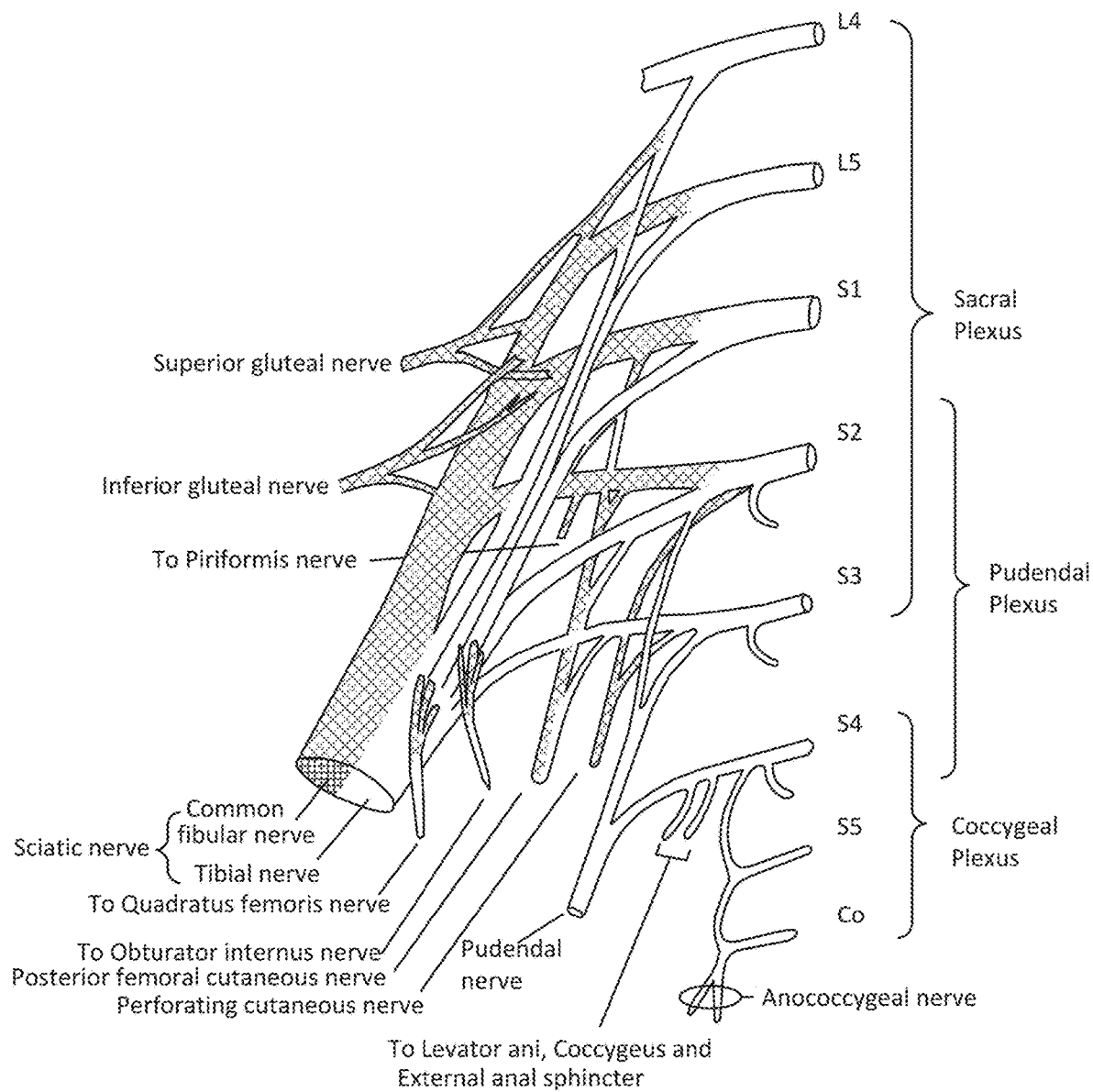

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, either visually, through the use of EMG as described herein or both, the physician can determine whether the targeted nerve is being stimulated. While stimulation at a certain threshold may trigger the noted muscle responses, stimulation at a subthreshold level may still provide stimulation to the nerve associated with the targeted organ without causing the corresponding muscle response, and in some embodiments, without causing any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder-related dysfunction, and in particular OAB.

FIG. 3 schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 30 that maintains a position of a set of neurostimulation electrodes 40 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

As shown in FIG. 3, the implantable pulse generator 10 is implanted in the lower back, upper buttock region of the patient. Patients are commonly instructed to position the charging device over a scar from the incision formed during implantation of the neurostimulator. However, the location of the scar in a sacral neurostimulation system implantation makes this task difficult, since the patient cannot readily observe the scar during placement of the charging device. Further, in some patients, the location of the neurostimulator may change over time, for example due to weight loss that tends to occur after successful treatment. Thus, by locating the alignment indicator feature within a user device, such as a clinician programmer, patient remote, or personal computing device of the patient, the alignment indicator can be communicated to the patient during manual positioning of the charging device, thereby allowing for precise placement without visually observing placement. It is appreciated that while the scar might fail to indicate a proper position for the charging device, it can be still be used as a reference with respect to the newly determined optimal position (e.g. 2 cm up/3 cm to the right from the scar), which can be communicated to the patient for subsequent charging sessions.

Properties of the electrical pulses can be controlled via a controller of the implanted pulse generator. In some embodiments, these properties can include, for example, the frequency, strength, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 4:
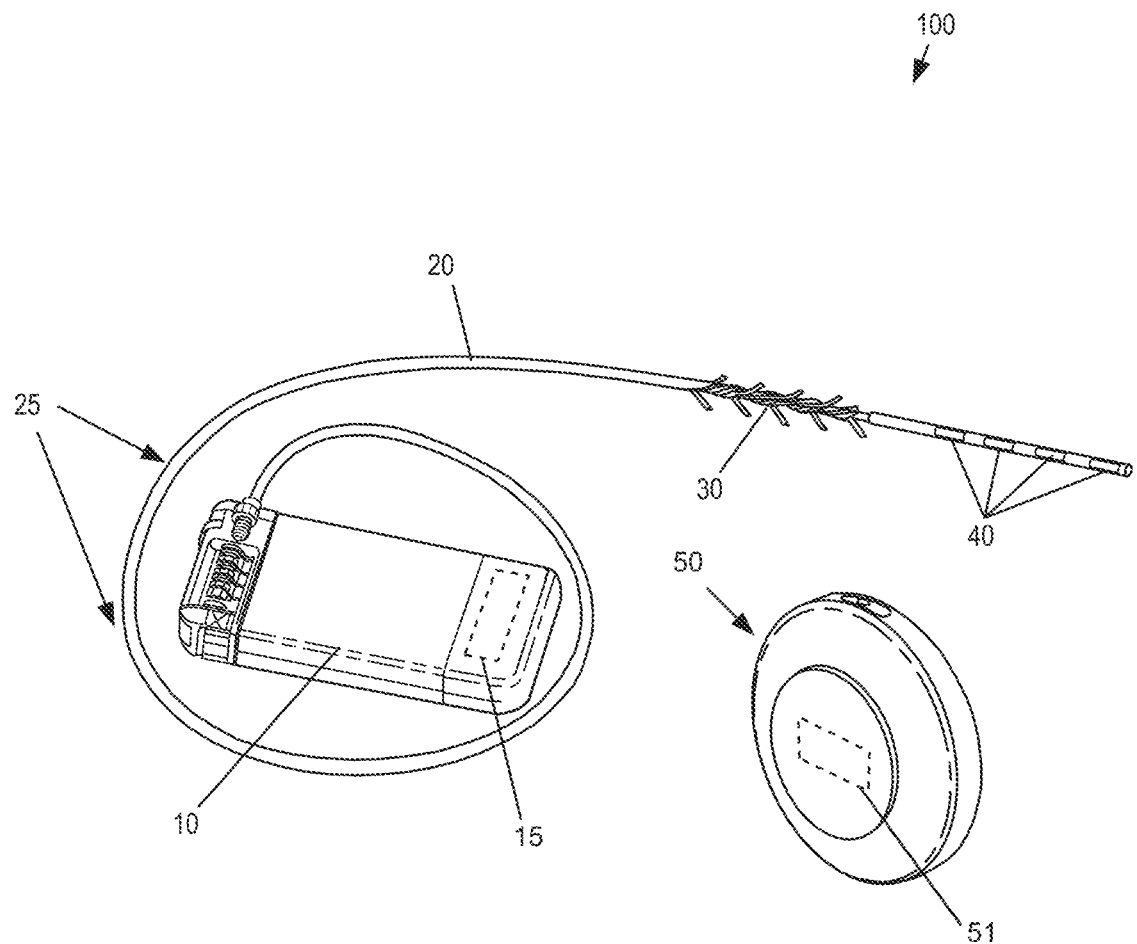
FIG. 4 shows an example of a neurostimulation system having an implantable stimulation lead, an implantable pulse generator, and an external charging device, in accordance with some embodiments.

FIG. 4 illustrates an example neurostimulation system 100 that is fully implantable and adapted for sacral nerve stimulation treatment. The implantable system 100 includes an IPG 10 that is coupled to a neurostimulation lead 20 that includes a group of neurostimulation electrodes 40 at a distal end of the lead and an internal receiving coil 15. The lead includes a lead anchor portion 30 with a series of tines extending radially outward so as to anchor the lead and maintain a position of the neurostimulation lead 20 after implantation. The lead 20 may further include one or more radiopaque markers 25 to assist in locating and positioning the lead using visualization techniques such as fluoroscopy. In some embodiments, the IPG provides monopolar or bipolar electrical pulses that are delivered to the targeted nerves through one or more neurostimulation electrodes, typically four electrodes. In sacral nerve stimulation, the lead is typically implanted through the S3 foramen as described herein.

In one aspect, the IPG is rechargeable wirelessly through conductive coupling by use of a charging device 50, which is a portable device powered by a rechargeable battery to allow patient mobility while charging. The charging device includes a charging coil 51 disposed within and is used for transcutaneous charging of the IPG through RF induction. The charging device 50 can either be either patched to the patient's skin using an adhesive or can be held in place using a belt 53 or by an adhesive patch 52. When recharging the IPG 10, the charging device 50 can be held in place using the belt 53 or adhesive patch 52 such that a surface 54 of the charging device 50 contacts the skin through which the IPG 10 is recharged, is parallel to the skin through which the IPG 10 is recharged, and/or is proximate to the skin through which the IPG 50 is recharged. In such position, the charging device axis, which can be perpendicular to the surface 54 can be perpendicular to the skin through which the IPG 10 is recharged. The charging device 50 may be charged by plugging the charging device directly into an outlet or by placing the charging device in a charging dock or station that connects to an AC wall outlet or other power source.

The charging device 50 can include a housing. The housing can comprise a variety of shapes and sizes. In some embodiments, the housing can be cylindrically shaped as shown in FIG. 4, and specifically, can comprise a plurality of connected cylindrical portions, wherein the connected cylindrical portions have different diameters and/or lengths. In some embodiments, the housing 51 can be a metal or polymer such as a plastic or the like.

The charging device 50 can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. The charging device 50 may include an energy storage feature, such as one or more capacitors, and typically includes a wireless charging unit. Some details of charging device 50 will be discussed at greater lengths below with respect to FIG. 7. The charging device can further include one or more positional sensors, such as an accelerometer, for determination of a relative position of the charging device and/or a direction of movement during repositioning.

The system may further include a patient remote 70 and clinician programmer 60, each configured to wirelessly communicate with the implanted IPG, or with the EPG during a trial. The clinician programmer 60 may be a tablet computer used by the clinician to program the IPG and the EPG. The device also has the capability to record stimulation-induced electromyograms (EMGs) to facilitate lead placement, programming, and/or re-programming. The patient remote may be a battery-operated, portable device that utilizes radio-frequency (RF) signals to communicate with the EPG and IPG and allows the patient to adjust the stimulation levels, check the status of the IPG battery level, and/or to turn the stimulation on or off.

Figure 5A:
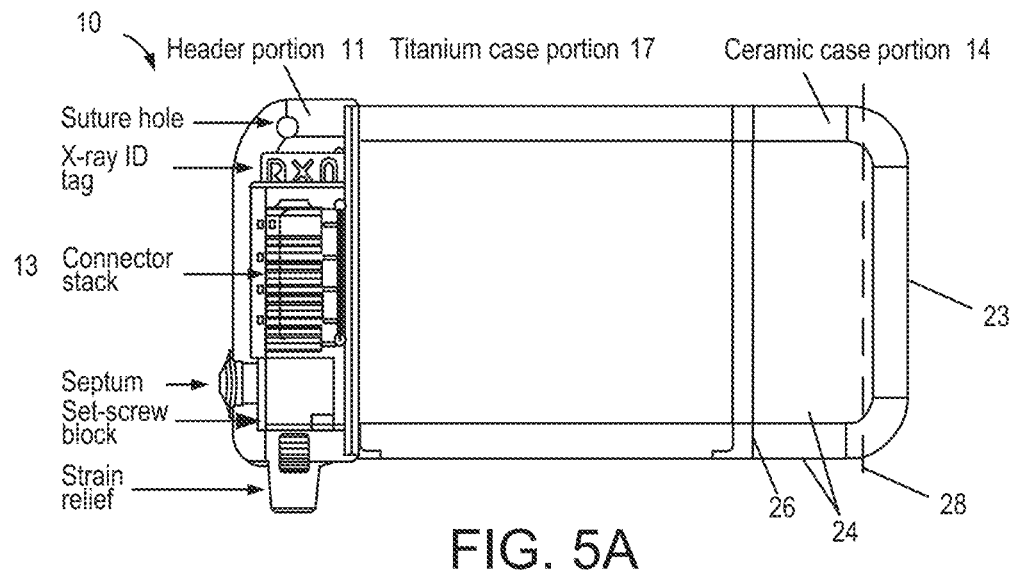
FIGS. 5A-5B show detail views of an implantable pulse generator and associated components for use in a neurostimulation system, in accordance with some embodiments.
Figure 5B:
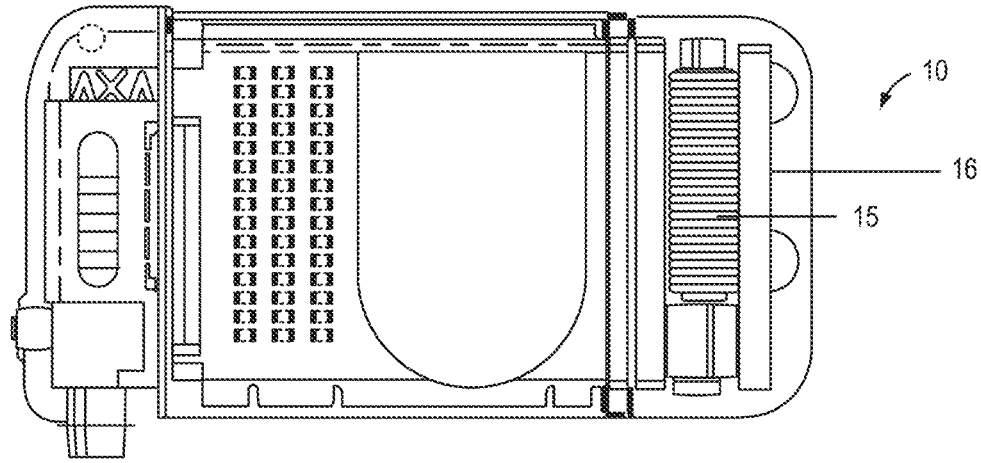

FIG. 5A-5B show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors, and typically includes a wireless charging unit.

One or more properties of the electrical pulses can be controlled via a controller of the IPG or EPG. In some embodiments, these properties can include, for example, the frequency, strength, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 10 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 µs to 500 µs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG may include a header portion 11 at one end and a ceramic portion 14 at the opposite end. The header portion 11 houses a feed-through assembly 12 and connector stack 13, while the ceramic case portion 14 houses an antennae assembly 16 to facilitate wireless communication with the clinician program, the patient remote, and/or a charging coil to facilitate wireless charging with the charging device. The remainder of the IPG is covered with a titanium case portion 17, which encases the printed circuit board, memory and controller components that facilitate the electrical pulse programs described above. The ceramic portion 14 includes an end 23, sides 24, and a connection portion 26 that connects the ceramic portion 14 to the case portion 17. In the example shown in FIG. 5B, the antennae assembly 16 is positioned such that a plane 28, in which loops of a radiating element lay, is perpendicular to and extends through the sides 24 of the ceramic portion 14.

In some embodiments, such as that shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG, and that ceramic may be used to form additional portions of the case.

In one aspect, utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and clinician programmer. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time.

In another aspect, the ferrite core is part of the charging coil assembly 15, shown in FIG. 5B, which is positioned inside the ceramic case 14. The ferrite core concentrates the magnetic field flux through the ceramic case as opposed to the metallic case portion 17. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. This configuration also allows the IPG to be effectively charged at a depth of 3 cm with the charging device, when positioned on a skin surface of the patient near the IPG, and reduces re-charging time.

Figure 6:
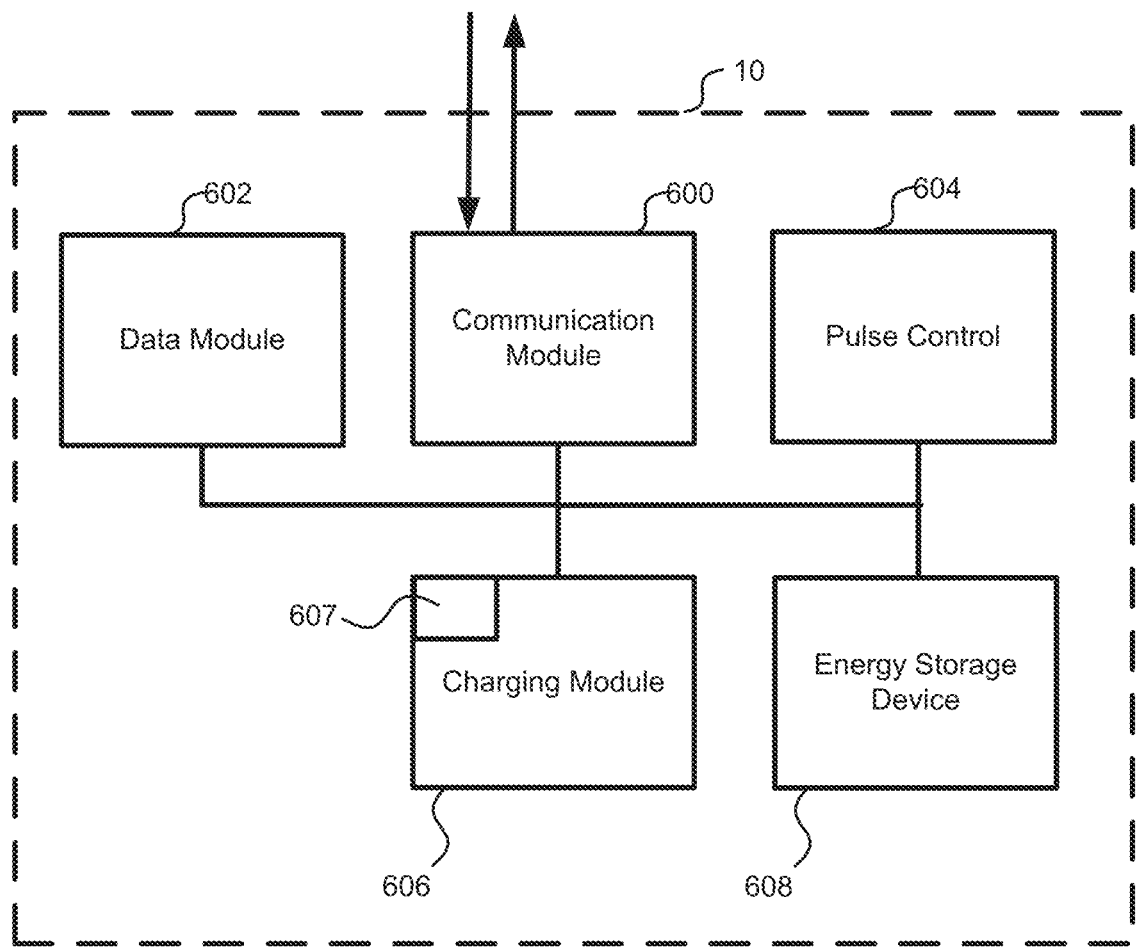
FIG. 6 shows a schematic illustration of one embodiment of the architecture of the IPG, in accordance with some embodiments.

FIG. 6 shows a schematic illustration of one embodiment of the architecture of the IPG 10. In some embodiments, each of the components of the architecture of the IPG 10 can be implemented using the processor, memory, and/or other hardware component of the IPG 10. In some embodiments, the components of the architecture of the IPG 10 can include software that interacts with the hardware of the IPG 10 to achieve a desired outcome, and the components of the architecture of the IPG 10 can be located within the housing.

In some embodiments, the IPG 10 can include, for example, a communication module 600. The communication module 600 can be configured to send data to and receive data from other components and/or devices of the exemplary nerve stimulation system including, for example, the clinician programmer 60, the charging device 50, and/or the patient remote 70. In some embodiments, the communication module 600 can include one or several antennas and software configured to control the one or several antennas to send information to and receive information from one or several of the other components of the IPG 10. In some embodiments, for example, when connecting with the charging device 50, the communications module 600 can be configured to send data identifying the IPG 10 and/or characterizing one or several attributes of the IPG 10. In some embodiments, this information can be, for example, a number uniquely identifying the IPG 10 such as, for example, a serial number, or the like. In some embodiments, this data can characterize one or several attributes of the IPG 10 such as, for example, the natural frequency of a charging module 606 of the IPG 10 and/or of one or several components of the charging module 606 of the IPG. In some embodiments, the IPG 10 can be configured to communicate one or more charging parameters to a user device during charging, including any of a clinician programmer, patient remote, or a portable patient computing device, on which an alignment indicator can be provided based on the one or more charging parameters.

The IPG 10 can further include a data module 602. The data module 602 can be configured to manage data relating to the identity and properties of the IPG 10. In some embodiments, the data module can include one or several databases that can, for example, include information relating to the IPG 10 such as, for example, the identification of the IPG 10, one or several properties of the IPG 10, or the like. In one embodiment, the data identifying the IPG 10 can include, for example, a serial number of the IPG 10 and/or other identifier of the IPG 10 including, for example, a unique identifier of the IPG 10. In some embodiments, the information associated with the property of the IPG 10 can include, for example, data identifying the function of the IPG 10, data identifying the power consumption of the IPG 10, data identifying the charge capacity of the IPG 10 and/or power storage capacity of the IPG 10, data identifying potential and/or maximum rates of charging of the IPG 10, and/or the like. In some embodiments, the information associated with the property of the IPG 10 can include, for example, data identifying the natural frequency of the IPG 10 and/or components thereof. In some embodiments, this information identifying the natural frequency can be generated at the time of the manufacture of the IPG 10.

The IPG 10 can include a pulse control 604. In some embodiments, the pulse control 604 can be configured to control the generation of one or several pulses by the IPG 10. In some embodiments, for example, this can be performed based on information that identifies one or several pulse patterns, programs, or the like. This information can further specify, for example, the frequency of pulses generated by the IPG 10, the duration of pulses generated by the IPG 10, the strength and/or magnitude of pulses generated by the IPG 10, or any other details relating to the creation of one or several pulses by the IPG 10. In some embodiments, this information can specify aspects of a pulse pattern and/or pulse program, such as, for example, the duration of the pulse pattern and/or pulse program, and/or the like. In some embodiments, information relating to and/or for controlling the pulse generation of the IPG 10 can be stored within the memory.

The IPG 10 can include a charging module 606. In some embodiments, the charging module 606 can be configured to control and/or monitor the charging/recharging of the IPG 10. In some embodiments, for example, the charging module 606 can include one or several features configured to receive energy for recharging the IPG 10 such as, for example, one or several inductive coils/features that can interact with one or several inductive coils/features of the charging device 50 to create an inductive coupling to thereby recharge the IPG 10. In some embodiments, the charging module 606 can include hardware and/or software configured to monitor the charging of the IPG 10 including, for example, the charging coil assembly 15, also referred to herein as the receiving coil assembly 15 or the elongate receiving coil assembly 15. In some embodiments, the software of the charging module can be updated periodically, for example in a software push through an external computing device in communication with the communication module. Typically, the communication module provides a secure, authentication of any communication regarding a software update such that any software update is communicated only if a secure, authenticated communication is received, for example, a communication from an authorized clinician programmer or a communication with an authorization key from a network or remote server.

The charging module 606 of the IPG 10 can include a charging circuit 607, also referred to herein as the resonant circuit 607, the secondary charging circuit 607, the secondary resonant circuit 607, the receiving charging circuit 607, or the receiving resonant circuit 607. In some embodiments, the charging circuit 607 can comprise, for example, at least one of: an inductor; a capacitor; or a resistor. The charging circuit 607 can be characterized by a natural frequency, which natural frequency can be determined at, for example, the time of assembly of the charging circuit 607 or after the implantation of the IPG 10 in the body. In some embodiments, because of the relatively constant temperature and environment in the body, the natural frequency of the charging circuit 607 can remain constant after the implantation of the IPG 10 into the body.

The IPG 10 can include an energy storage device 608. The energy storage device 608, which can include the energy storage features, can be any device configured to store energy and can include, for example, one or several batteries, capacitors, fuel cells, or the like. In some embodiments, the energy storage device 608 can be configured to receive charging energy from the charging module 606.

Figure 7:
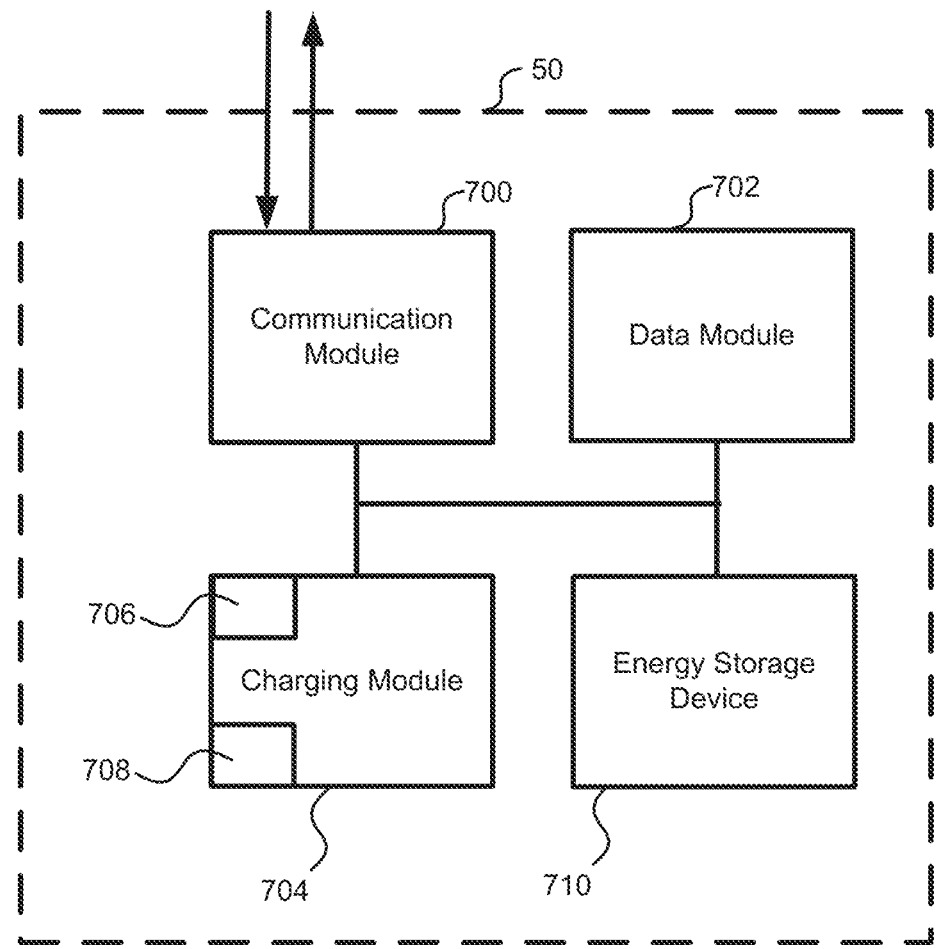
FIG. 7 shows a schematic illustration of one embodiment of the architecture of the charging device, in accordance with some embodiments.

FIG. 7 shows a schematic illustration of one embodiment of the architecture of the charging device 50. In some embodiments, each of the components of the architecture of the charging device 50 can be implemented using the processor, memory, and/or other hardware component of the charging device 50. In some embodiments, the components of the architecture of the charging device 50 can include software that interacts with the hardware of the charging device 50 to achieve a desired outcome, and the components of the architecture of the charging device 50 can be located within the housing 51.

In some embodiments, charging device 50 can include, for example, a communication module 600. The communication module 700 can be configured to send data to and receive data from other components and/or devices of the exemplary nerve stimulation system including, for example, the clinician programmer 60, the IPG 10, and/or the patient remote 70. In some embodiments, the communication module 700 can include one or several antennas and software configured to control the one or several antennas to send information to and receive information from one or several of the other components of the charging device 50. In some embodiments, the charging device communicates with the IPG during charging with a first antennae and communicates one or more charging parameters or associated metric to the user device by a second antenna. In some such embodiments, the first antenna can communicate with the IPG by MedRadio, while the second antenna communicates with the user device by Bluetooth. In some embodiments, when connecting with the IPG 10, the communications module 700 can be configured to receive data identifying the IPG 10 and/or characterizing one or several attributes of the IPG 10. In some embodiments, this information can be, for example, a number uniquely identifying the IPG 10 such as, for example, a serial number, or the like.

The charging device 50 can further include a data module 702. The data module 702 can be configured to manage data relating to the identity and properties of the IPG 10. In some embodiments, the data module can include one or several database that can, for example, include information relating to the IPG 10 such as, for example, the identification of the IPG 10, one or several properties of the IPG 10, or the like. In one embodiment, for example, the data module can comprise a database including one or several IPG 10 identifiers such as serial numbers for those one or several IPGs 10. In some embodiments, the data module 702 can further include characterization data associated with some or all of the one or several IPGs 10 identified in the data module 702. In some embodiments, for example, this characterization data can include the identification of the natural frequency of charging circuit 607 of the IPG 10. In some embodiments, this characterization data can be received from the IPG 10 and/or can be generated by the charging device 50 in response to interactions with the IPG 10. In some such embodiments, the data modules provides segregation of data, for example, between charging parameters utilized during charging control and charging parameters sent to a user device. Such an approach may allow the user device to access data and processes that would not otherwise be feasible or recommended, to avoid unauthorized access to charging control operations by the patient or clinician.

The charging device 50 can include a charging module 704. In some embodiments, the charging module 704 can be configured to control and/or monitor the charging/recharging of the IPG 10. In some embodiments, for example, the charging module 704 can include one or several features configured to provide energy for recharging the IPG 10 such as, for example, one or several inductive coils/features that can interact with one or several inductive coils/features of the IPG 10 to create an inductive coupling to thereby recharge the IPG 10. In some embodiments, the charging module 704 can include hardware and/or software configured to monitor the charging of the IPG 10 including, for example, the charging coil assembly 15.

The charging module 704 of the charging device 50 can include a charging circuit 706, also referred to herein as the resonant circuit 706, the primary charging circuit 706, the primary resonant circuit 706, the transmitter charging circuit 706, or the transmitter resonant circuit 706. In some embodiments, the charging circuit 706 can comprise, for example, at least one of: an inductor; a capacitor; or a resistor. In some embodiments, the resonant circuit 706 can comprise the sending coil assembly, also referred to herein as a transmitting coil assembly or a primary coil assembly.

In some embodiments, the charging module 704 can include a driver 708. The driver 708 can be, for example, a non-class E driver, and in some embodiments, the driver 708 can be a class E driver, and specifically can be a microprocessor controlled class E driver as disclosed in U.S. patent application Ser. No. 14/446,294, filed on Jul. 29, 2014, the entirety of which is hereby incorporated by reference herein. In some embodiments, the driver 708 can be configured to provide electrical pulses to the resonant circuit 706 to thereby charge the IPG 10. In some embodiments, the driver 708 can be further configured to provide these pulses at a frequency corresponding to the natural frequency of the resonant circuit 706. Thus, in some embodiments, the natural frequency of the resonant circuit 706 of the charging device 50 can be determined by determining the frequency with which the driver 708 is providing pulses to the resonant circuit 706.

The charging device 50 can include an energy storage device 710. The energy storage device 710 can be any device and/or features configured to store energy and can include, for example, one or several batteries, capacitors, fuel cells, or the like. In some embodiments, the energy storage device 710 can be configured to provide charging energy to the charging module 704 for charging of the IPG 10.

In some embodiments, for example in which the IPG 10 is implanted such that at least one of axes 802, 809 is parallel and/or substantially parallel with the skin surface closest to the IPG 10 and/or from which charging of the IPG 10 is intended, the use of a planar winding 852 in the charging device 50 combined with an elongate winding 800 in the IPG 10 can eliminate the need to control the rotational orientation of the charging device 50 with respect to the IPG 10. This can simplify the positioning of the charging device 50 with respect to the IPG 10. Specifically, the effect of the relative rotational orientation of the charging device 50 with respect to the IPG 10 is diminished when the IPG 10 and the charging device 50 have a relative orientation such that the axes 802, 809 of the charging circuit 15 of the IPG 10 are nonparallel to the winding axis 854 and/or the core axis 864, and/or have a relative orientation such that the axes 802, 809 of the charging circuit 15 of the IPG 10 are perpendicular and/or substantially perpendicular to the winding axis 854 and/or the core axis 864. In such an embodiment, effective energy transfer between from the charging device 50 to the IPG 10 can be achieved by positioning the charging device 50 proximate to the IPG 10 without having to also controlling the rotational orientation of the charging device 50 about the charging device axis 55. As rotational orientation of the charging device 50 does not need to be controlled, the positioning of the charging device 50 for recharging of the IPG 10, and thus recharging of the IPG 10 is simplified.

As a part of positioning, or subsequent to positioning of the charging device 50 with respect to the IPG 10, the charging device 50 can power the sending coil assembly 850, and specifically, the charging module 704 can power the sending coil assembly 850. In some embodiments, this powering of the sending coil assembly 850 can comprise the generation of series of pulses by the driver 708, the pulses timed to cause resonance in the charging circuit 706. These pulses can be delivered to the charging circuit 706 and can generate resonance in the charging circuit 706 at the resonant frequency of the charging circuit 706 and/or at another desired frequency. Through this powering of the charging circuit 706, and the current oscillations at the charging circuit 706, a magnetic field can be generated by the sending coil assembly 850. The magnetic field can be directed away from the circuitry 870 of the charging device 50 by the core 862 of the sending coil assembly 850. The magnetic field can be generated until the charging device 50 determines to terminate charging of the IPG 10 and/or until the charging device 50 is instructed to terminate charging of the IPG 10. Thus, the charging operation during which positioning of the charging device is performed can be standard operating charging, or can be a modified charging operation especially suited for placement of the charging device, for example, as described above.

Figure 8:
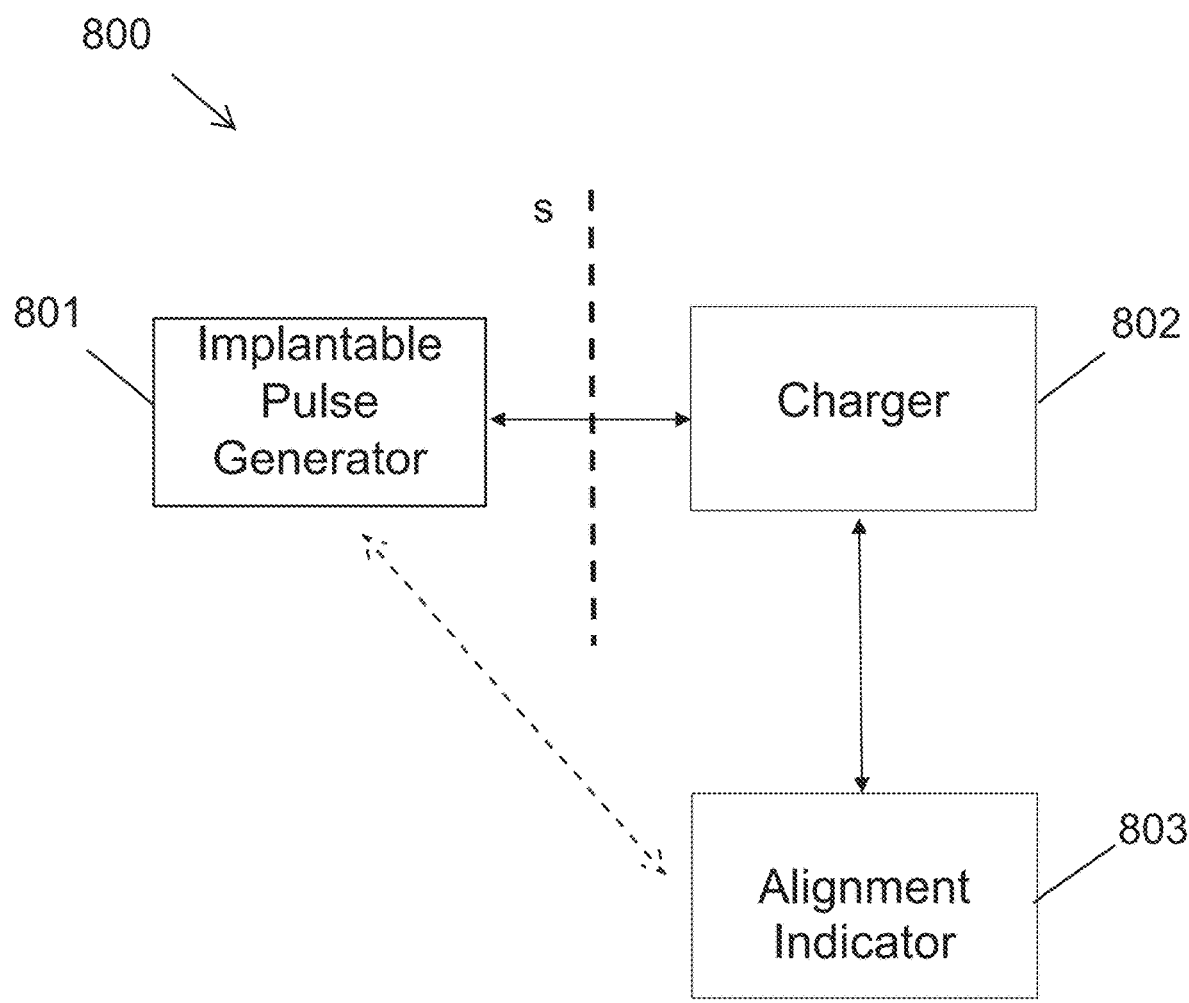
FIG. 8 shows a schematic illustration of communication between an IPG and charging device and an alignment indicator, in accordance with some embodiments.

FIG. 8 shows a schematic illustration of a system 800 having an IPG 80, charging device 802 and an alignment indicator 803, in accordance with some embodiments. In this embodiment, the charging device 802 communicates directly with the implantable pulse generator 801 across the patient's skin to facilitate controlled transcutaneous energy transfer between the charging device and implantable device. Typically, this transcutaneous communication is performed by shortwave radio transmissions (e.g. MedRadio). The charging device 801 then communicates one or more charging parameters to the alignment indicator 803, which can be displayed on a user interface of one or more external computing devices or can be integrated within the charging device itself. Typically, this latter communication is by another type of shortwave radio transmission (e.g. Bluetooth). In some embodiments, the alignment indicator utilizes information obtained only from the charging device, which includes charging parameters from both the charging device and the implantable pulse generator during charging. In some embodiments, the alignment indicator can also include information obtained directly from the implantable pulse generator, or information obtained from both.

Figure 9:
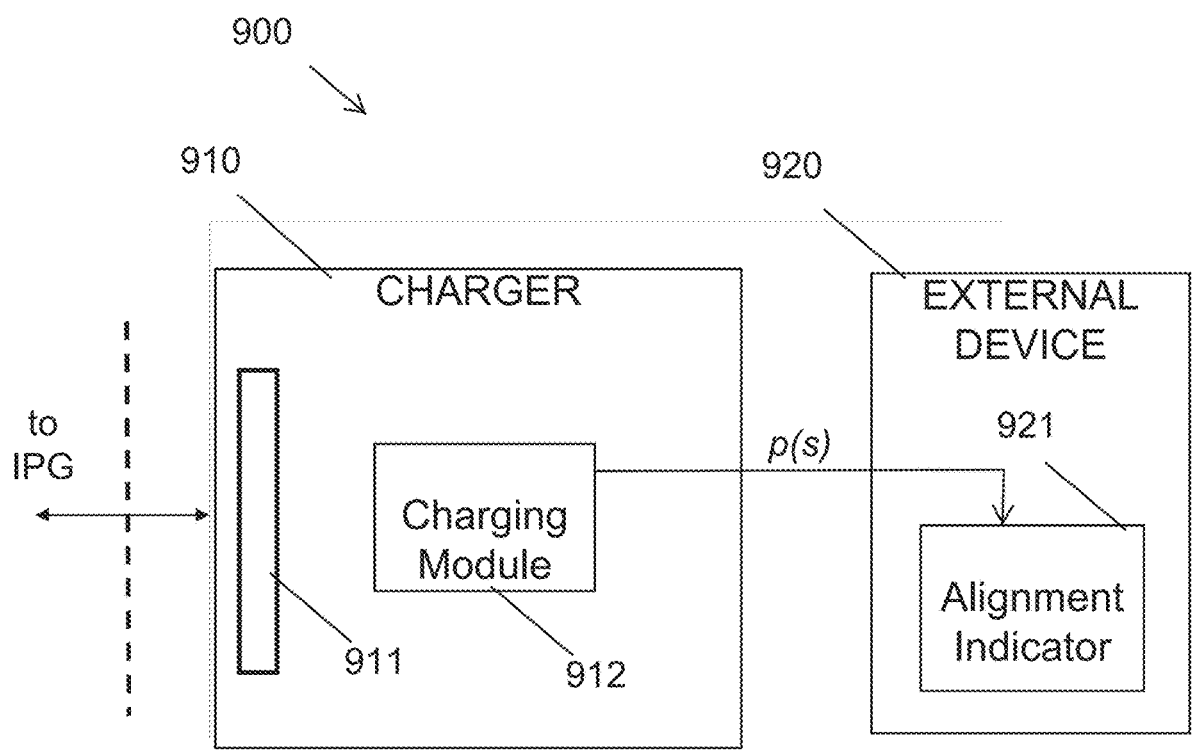
FIG. 9 shows a schematic illustration of a charging device communicating with an external device having an alignment indicator, in accordance with some embodiments.

FIG. 9 shows a schematic illustration of system 900 having a charging device 910 with a charging coil 911 and charging module 912 having circuitry and a processor configured to control transcutaneous charging with the IPG. The charging module 912 is further configured to communicate one or more charging parameters, p(s), during charging to an external device 920 upon receiving a request from the external device. The external device 902 indicates alignment on a user interface as alignment indicator 921. The indicator can include any of an audio, visual, or haptic output on the user interface of the external device 920. In some embodiments, the external device 920 is associated with the clinician (e.g. clinician programmer), while in other embodiments, the external device 920 can be associated with the patient (e.g. patient remote, smartphone, table). In this embodiment, the alignment indicator can be a display of the charging parameters or associated metric obtained directly from the charging module (e.g. charging signal strength, charging efficiency, current, voltage, etc.). In some embodiments, these parameters or metric can be a parameter or metric that is already obtained and determined by the charging module during standard charging operation such that further processing of the parameters or metric by the external device is not required.

Figure 10:
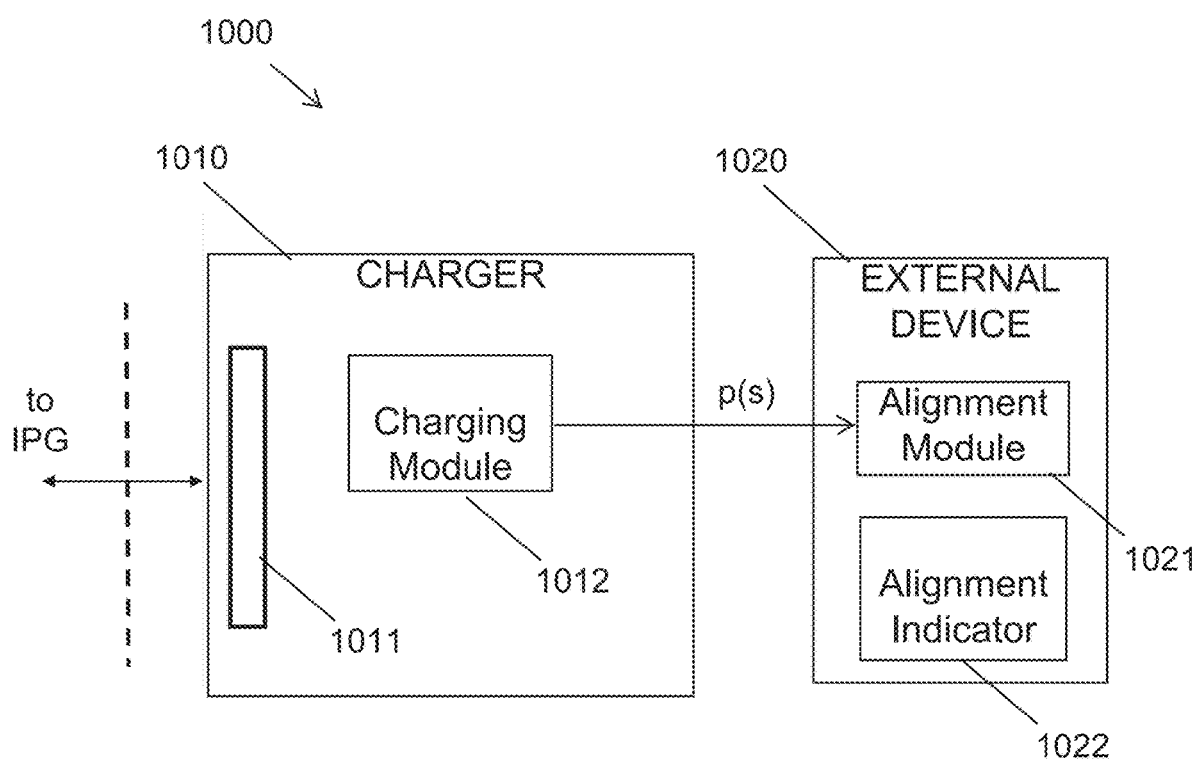
FIGS. 10-11 show schematic illustrations of charging devices communicating with external devices having an alignment indicator, in accordance with some embodiments.

FIG. 10 shows a schematic illustration of system 1000 having a charging device 1010 with a charging coil 1011 and a charging module 1012 having circuitry and processor configured to control transcutaneous charging with the IPG. The charging module 912 is further configured to communicate one or more charging parameters, p(s), during charging to an external device 1020. The external device 1020 indicates alignment on a user interface as alignment indicator 1022. The indicator can include any of an audio, visual, or haptic output on the user interface of the external device 920. In some embodiments, the external device 1020 is associated with the clinician (e.g. clinician programmer), while in other embodiments, the external device 1020 can be associated with the patient (e.g. patient remote, smartphone, table). In this embodiment, the external device further includes an alignment module 1021 that is configured to receive the charging parameters and process the parameters into a useful metric, such as charging efficiency, or to determine the suitable alignment indicator based on the charging parameters.

Figure 11:
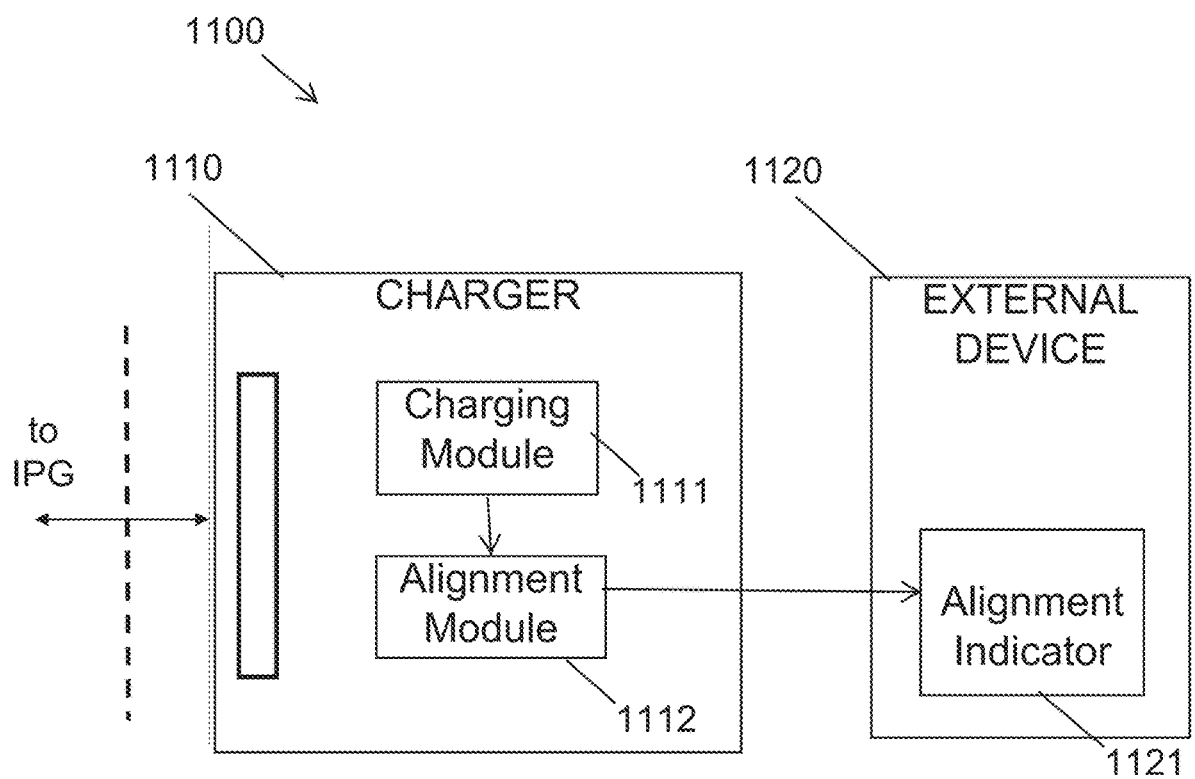

FIG. 11 shows a schematic illustration of a charging device 1110 having a charging module 111 and external device 1120 with alignment indicator 1121, that operate substantially similar to that in FIG. 10, except the alignment module 1112 is included within the charger 1110. In some embodiments, this functionality is provided by a software push update to the charger from the external device.

Figure 12:
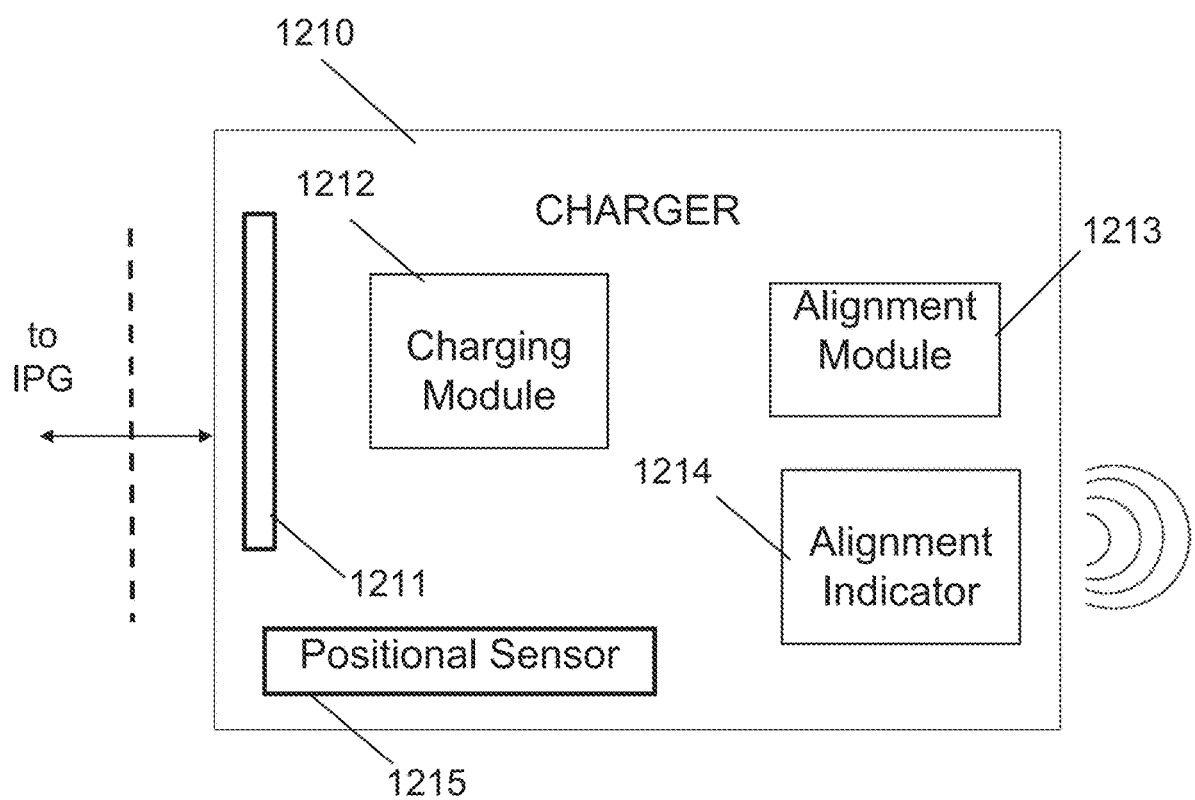
FIG. 12 shows a depiction of a charging device having an integrated alignment indicator and positional sensor, in accordance with some embodiments.

FIG. 12 shows a schematic illustration of a charging device integrated with the alignment indicator. Charger 12010 includes a charging module 121, alignment module 1213 and alignment indicator 1214 that operates in a similar manner as in previous embodiments, except the output of the alignment indicator is provided by the charger itself. The indicator can include any of an audio, visual, or haptic output on the user interface of the external device 920. In some embodiments, the indicator is an audio output, such as a series of beeps or tones, or audio verbal instructions to the user. In this embodiment, it may be advantageous to use different types of indicator alerts or an adaptive alert based on the charging parameters, for example, a series of beeps that increase in frequency as the charging efficiency increases and/or changes to a sustained beep when maximum charge efficiency is detected to indicate the optimal charging device position.

In another aspect, the charging device can include one or more positional sensors 1215, such as an accelerometer, the output from which can be used to determine a relative position or movement of the charging device during manual positioning of the charging device. It is appreciated that this aspect can be included in any of the embodiments described herein. The output from the one or more sensors can be utilized to determine specific directional guidance to the user or clinician, for example, instruction to move the charging device upwards, left or right to improve alignment. In some embodiments, the sensor can be identify a rotational orientation of the charging device so that a user can receive instruction to rotate the charging device in order to further align corresponding coils. It is noted that the adhesive attachment device and belt allow for rotation of the charging device while supported within, as described in U.S. Pat. No. 10,682,521, which is incorporated herein by reference in its entirety. In some embodiments, the attachment device can further include one more sensors so that a relative position and/or orientation of the charging device within can be determined from the sensor positional output.

In another aspect, the invention pertains to specialized application configured to operate on an external computing device in communication with the charging device and/or implantable pulse generator. In some embodiments, the external computing device can be any of a clinician programmer, a patient remote or other specialized medical equipment associated with the neurostimulation system. In some embodiments, the external computing device can be a standard computing device of the clinician or the patient, such as a smartphone, tablet, laptop, or desktop computer, where the functionality to perform the methods described herein are provided, at least in part, by operation of the specialized application embodied by executable instructions recorded on a memory of the device.

FIGS. 13-18 shows example screen views of a user device within a specialized application having an alignment indicator within a clinician programmer, in accordance with some embodiments. The specialized application executes a charging device alignment procedure by which the clinician can observe fine-tuned alignment while the clinician or patient manually adjusts the position of the charging device. It is appreciated that this procedure can be used during initial setup of the system with the patient, and as needed, or at any subsequent time the patient experiences sub-optimal charging performance, migration of the implanted charger or significant weight loss.

Figure 13:
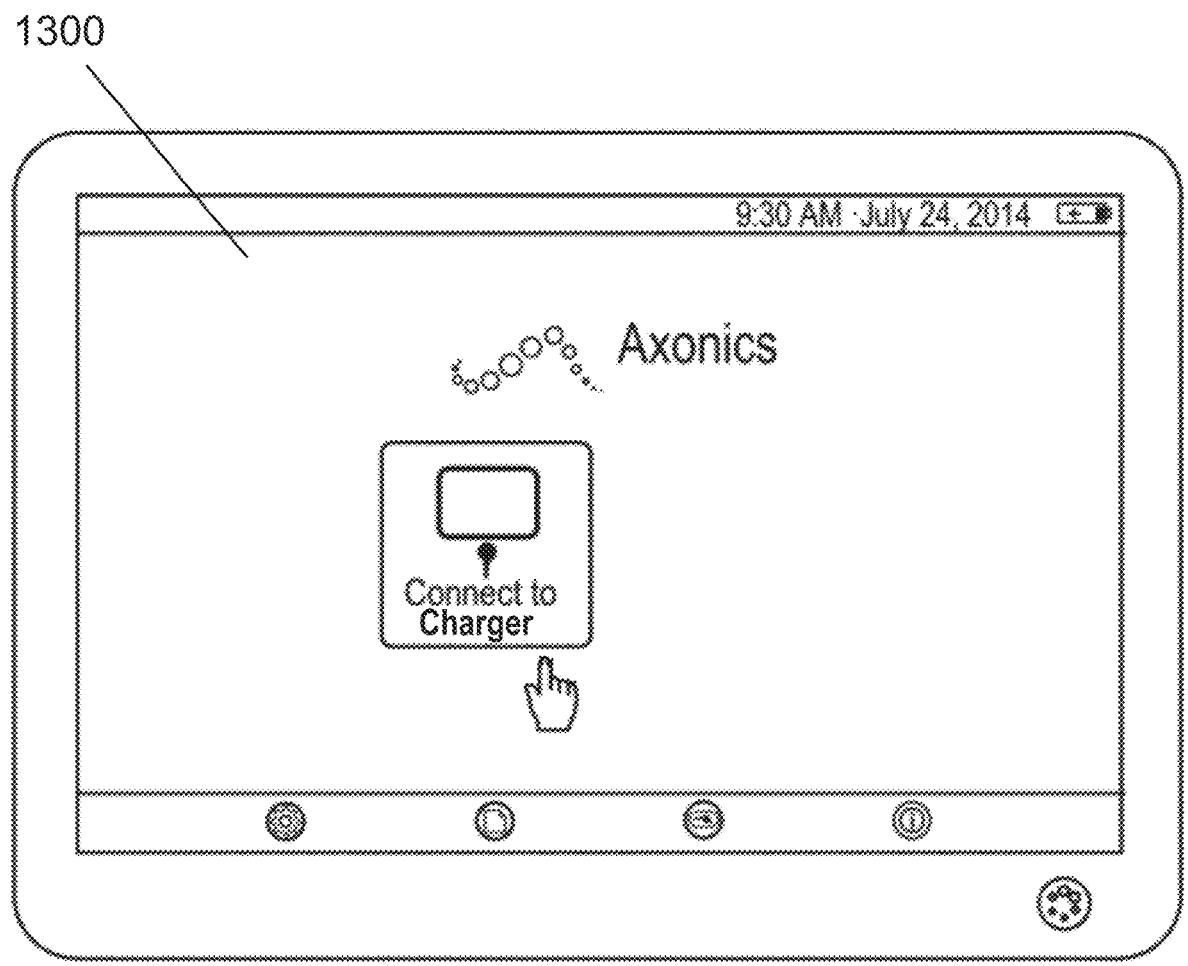
FIG. 13-18 shows example screen views of a user device performing a fine-tuned charging device by use of a specialized alignment application, in accordance with some embodiments.

As shown in FIG. 13, the clinician programmer initiates a fine-tuned charging device alignment procedure by selection on a user interface display 1300, which communicatively couples with the charging device. The clinician programmer includes an antenna that wirelessly communicates with an antenna in the charging device. Typically, the devices communicate by short-wavelength UHF radio waves, such as Bluetooth. The charging device and clinician programmer establish secure communication by an authorization procedure or handshake, for example, by exchanging identifying information between the clinician programmer to ensure the charging device is communicating with an authorized device and ensure the information from the charging device is secure.

Figure 14:
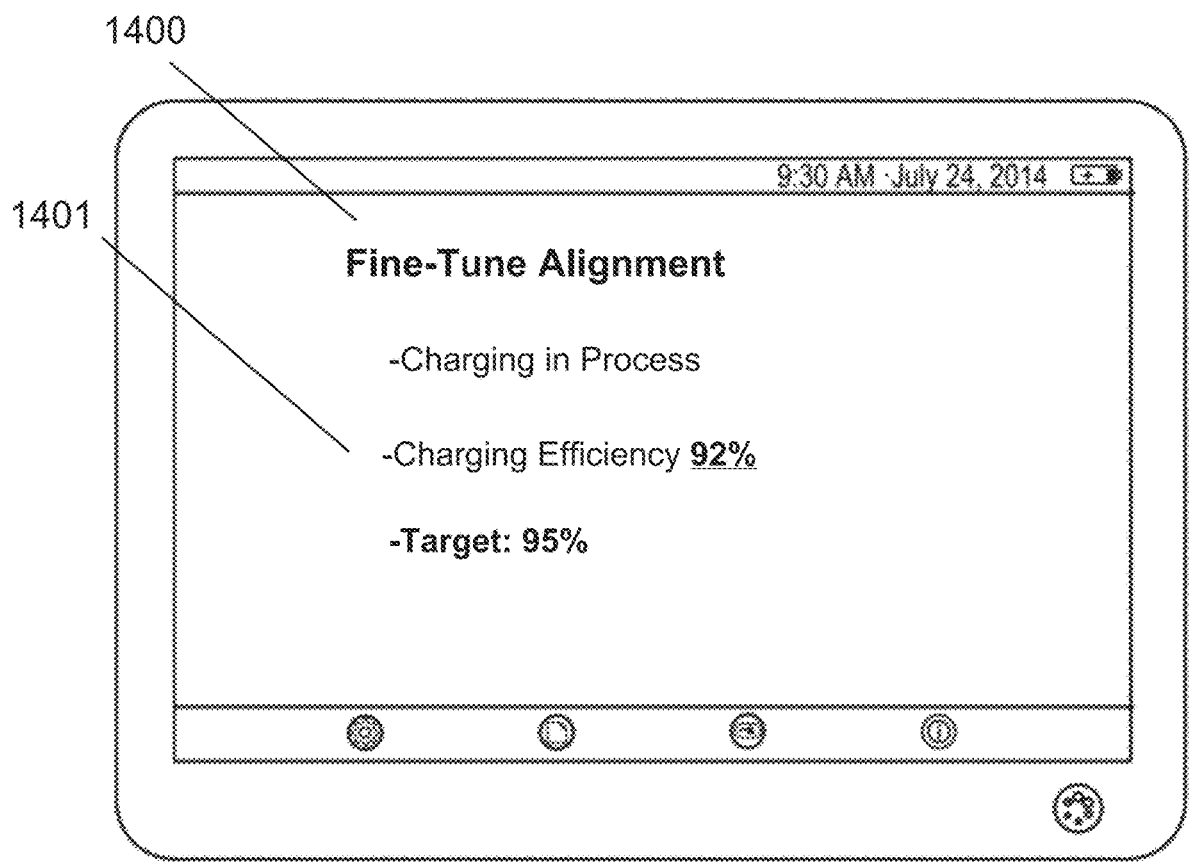

As shown in FIG. 14, the clinician procedure outputs a screen display 1400 for fine-tuned alignment that includes an alignment indicator 1401 on the graphical user interface display of the clinician to facilitate fine-tuned alignment of the charging device during charging. As the charging device performs a charging operation, the interfaces displays the alignment indicator in real-time, which is constantly updated while the patient or clinician manually adjust the charging device to allow the clinician and patient to determine the optimal position of the charging device. In this embodiment, the indicator 1401 is a dynamically updated display of charging efficiency. The charging efficiency can be determined from corresponding charging parameters already obtained by the charging device during charging. For example, the charging efficiency can be determined by comparing a power output of the charging device to the charging power generated in the implanted medical device. By observing the charging efficiency while manually adjusting the charging device through a range of suitable positions during which charging occurs, alignment between the coils of the charging device and the implanted device can be fined tuned to locate the optimal charging position. Once the optimal position is found, it's location can be noted by the clinician, by notes of the clinician made in the clinician programmer and/or by a photo taken by the clinician programmer and stored on the clinician programmer and subsequently communicated to the patient. The optimal position information can be stored by the clinician programmer and associated with the patient, so that the patient can access the optimal position information at a later date so that the patient can continue to replicate this optimal position during subsequent charging session.

Figure 15:
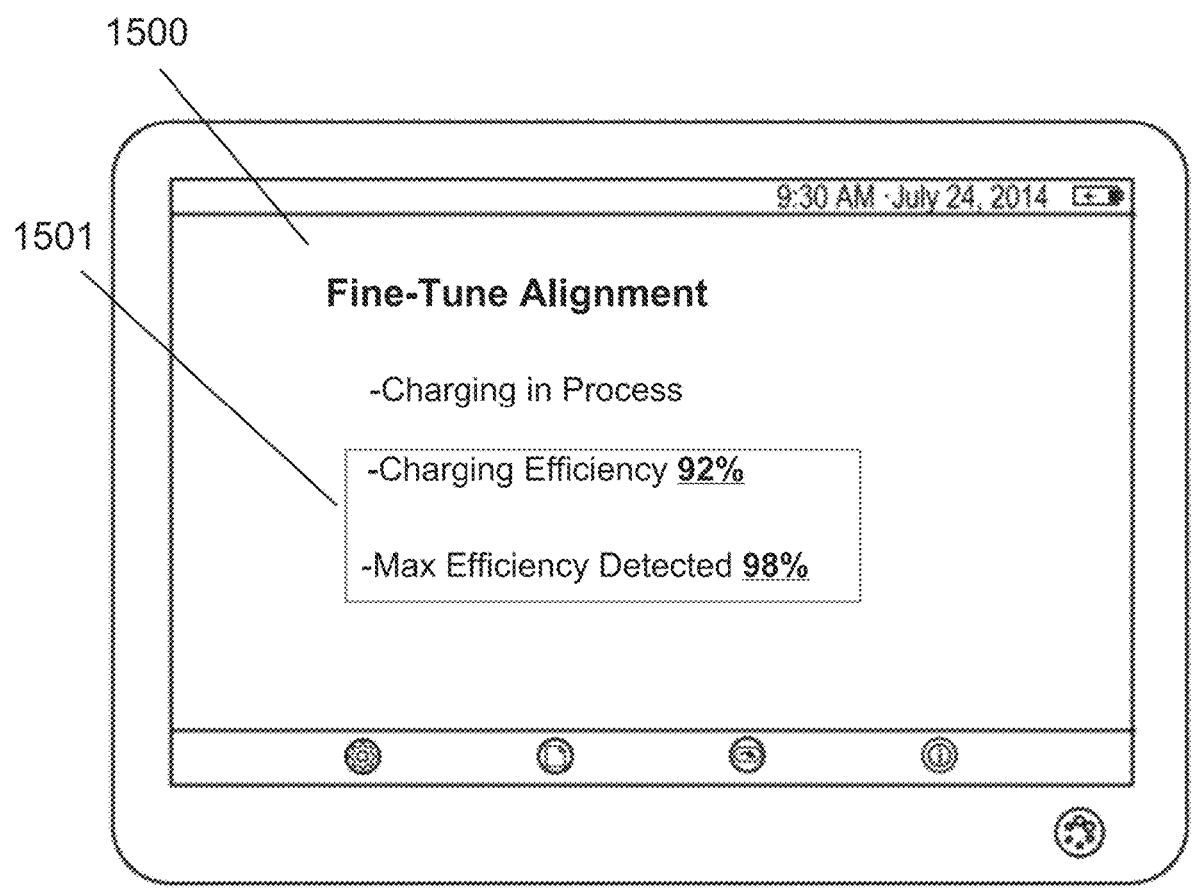
Figure 16:
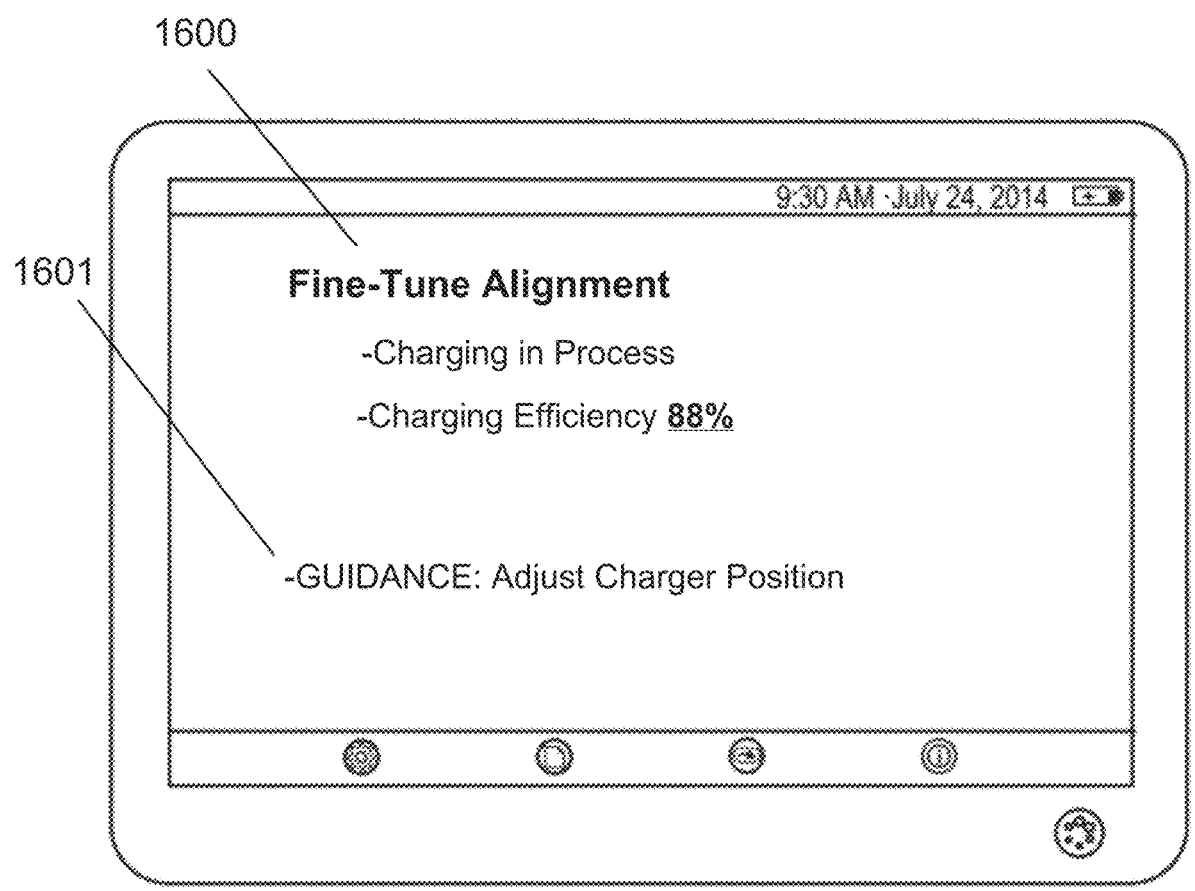

As shown in FIG. 15, the clinician programmer display 1500 with alignment indicator 1501 can also display the maximum or peak charging efficiency detected during the alignment procedure so that the clinician and patient can readily identify when the optimal position is reached. It is appreciated that this information can be communicated by various other means, for example, by a specialized charging metric unique to the neurostimulation system, a simplified rating system (1 through 5) that rates charging efficiency, or by audio alerts (e.g. instructions, beeps, tones), or any suitable means. In some embodiments, the indicator 1501 can include an additional indication (e.g. alert, beep, tone) when the current charging efficiency is at the maximum or target charging efficiency detected. In some embodiments, the clinician programmer is configured (e.g. via the specialized application) to determine a target value and/or range for the alignment indicator. The value can be one or more charging parameters, a relationship between parameters (e.g. efficiency), or a quantitative measure (e.g. ranking, scale, etc.) In some embodiments, this target value and/or range is determined a function of any of: the history of alignment indicator values; the history of one or more charging parameters; and an associated charging metric. In some embodiments, the history used for determining the target value and/or range is from a given charging session. In other embodiments, the history is from multiple sessions (e.g. 2 or more sessions, a set number of most recent sessions (e.g. 3, 4, 5), all charging sessions over a selected period of time (e.g. weeks, months, years), or all prior charging session. In some embodiments, the target range is less than a total range of values determined in a charging session. In some embodiments, the software application on the user device is configured to compile and/or analyze historical data of alignment indicators from multiple charging sessions and output the history of alignment indicators as a chart or other visual to the user, and/or determine trends on changes in alignment and charging parameters. This can be utilized to identify changes in position of the implanted medical device over time or changes in device performance necessitating intervention by the clinician, provider or device manufacturer. As shown in FIG. 16, the clinician programmer display 1600 with alignment indicator can further include instructions or guidance 1601 to the clinician or patient to further facilitate fine-tuned alignment. For example, if the current charging efficiency indicates that charging is suboptimal, the guidance can instruct the clinician or patient to further adjust the charger position.

Figure 17:
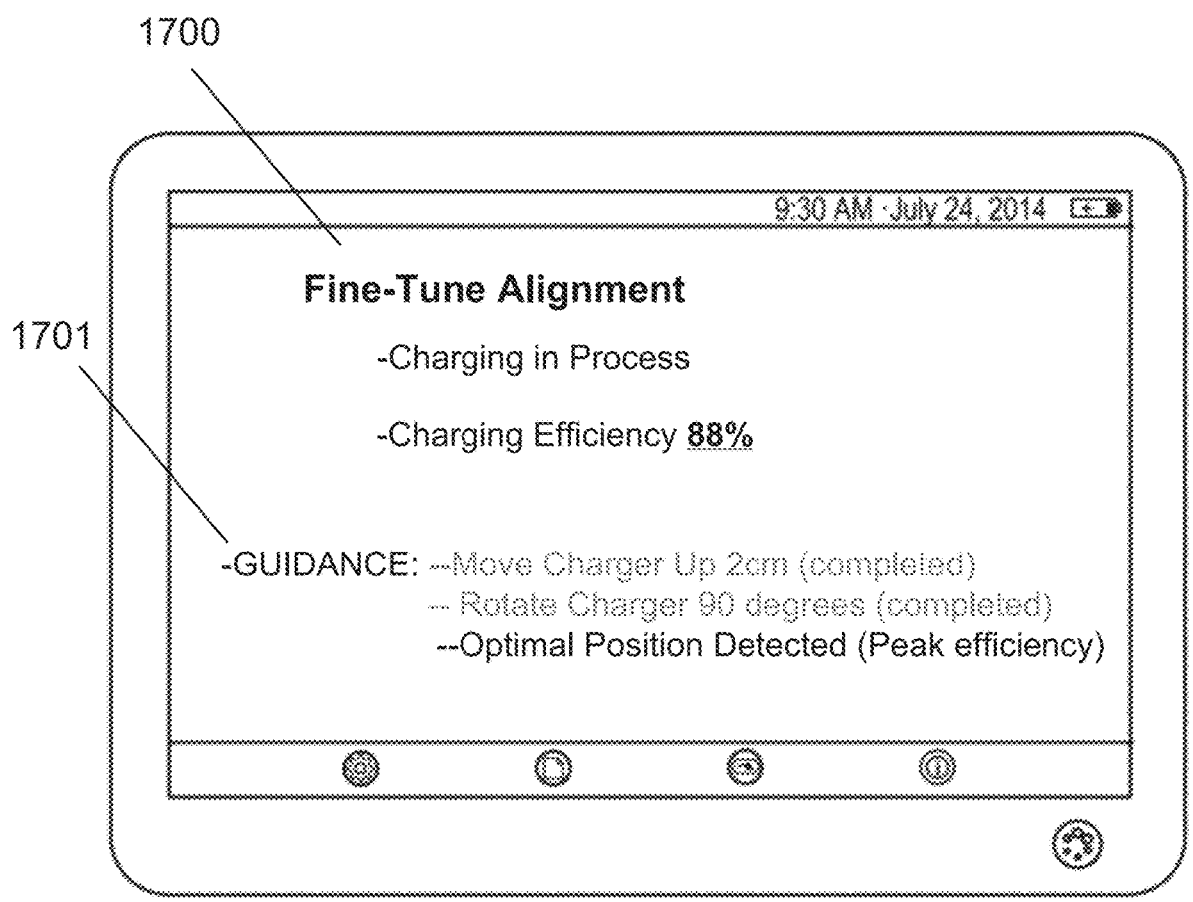

As shown in FIG. 17, the clinician programmer display 1700 with alignment indicator can further include directional instructions or guidance 1701. The directional guidance can include specific instructions as to how the charging device should be adjusted, for example, instructions to move the charging device up/down/left/right by a suggested distance, or by rotating the charging device. This guidance can be informed by a positional sensors disposed on the charging device, such as one or more accelerometers, as described herein. The guidance can then indicate to the user when the optimal position is detected.

Figure 18:
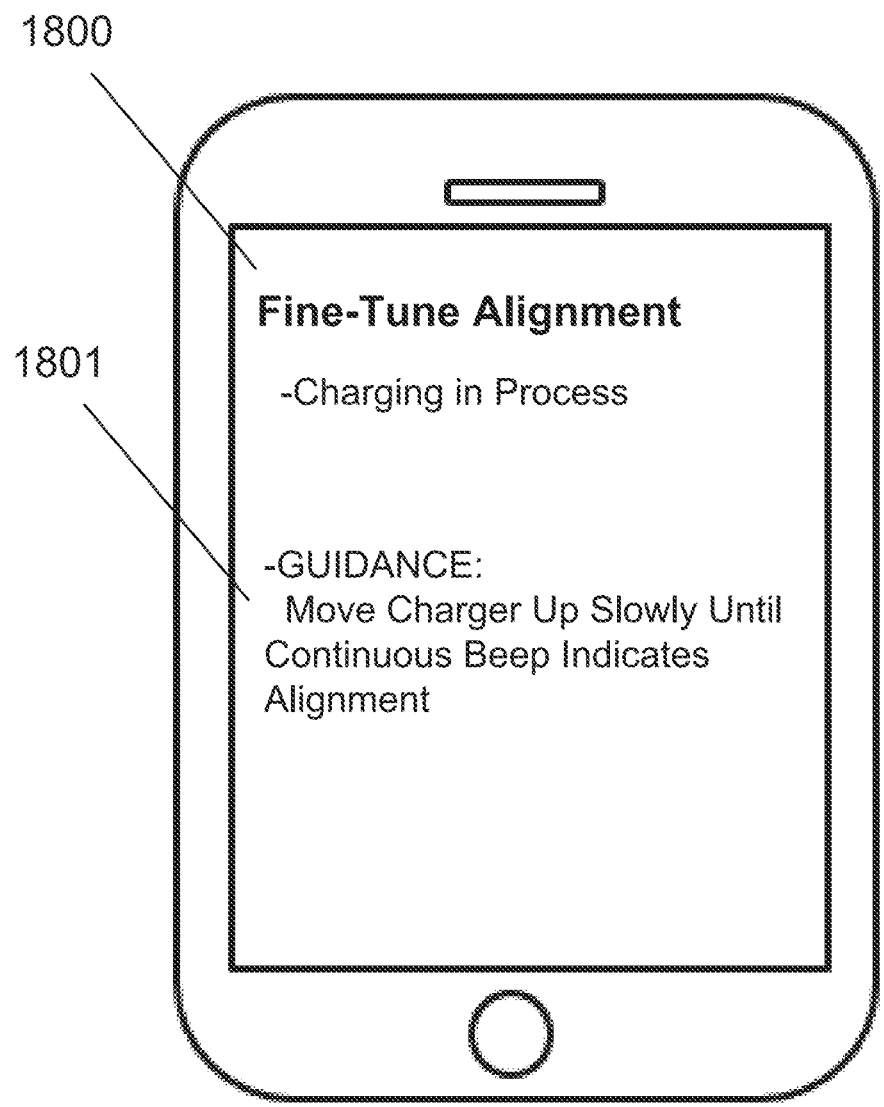

As shown in FIG. 18, the fine-tuned alignment procedure can be performed on a patient's device (e.g. smartphone) 1800 and can include any of the features of the alignment procedure described herein. In this embodiment, the alignment indicator includes directional guidance 1801, which can be provided in conjunction with an audio alert. For example, audio instructions for the user to move the charging device (e.g. move device left/right/up/down slowly or by an estimated distance). In some embodiments, the alert can change during adjustment of the charging device so that the patient can identify when the optimal position is reached, for example, beeping that increases as charging efficiency increases and changes to a continuous beep when the maximum efficiency is detected.

This approach has the advantages of allowing the patient to fine-tune charging device placement in a home setting as needed. In some embodiments, the patient can perform fine-tuned charging by use of the specialized application on their own device. In other embodiments, the patient's device can communicate with both the charging device and a clinician programmer through a network such that the clinician can facilitate fine-tuned adjustment remotely through the patient's device. In some embodiments, the fine-tuned alignment procedure can be automatically, at least partly, initiated when charging becomes deficient. For example, if routine charging becomes increasingly deficient, for example, as a patient loses weight, the patient's personal computing device (e.g. smartphone, tablet) can initiate a suggestion or alert to the patient to perform the fine-tuned alignment of the charging device and either lead the patient through the procedure on their personal computing device, or facilitate the procedure being performed remotely by the clinician or health care provider utilizing the user's personal computing device communicating with the clinician's computing device through a remote server or network.

Figure 19:
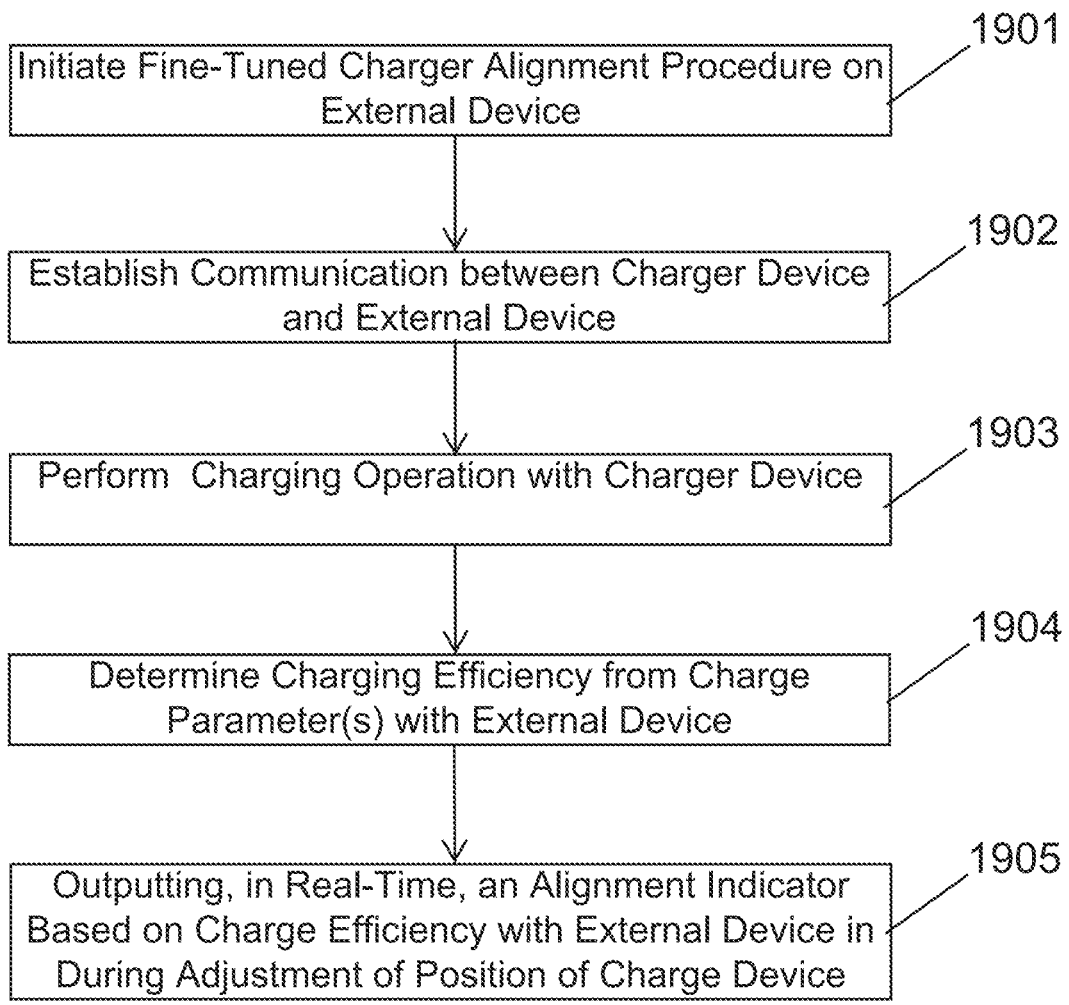
FIG. 19-20 shows exemplary methods of charging an implanted device with a charging device and an alignment indicator, in accordance with some embodiments.
Figure 20:
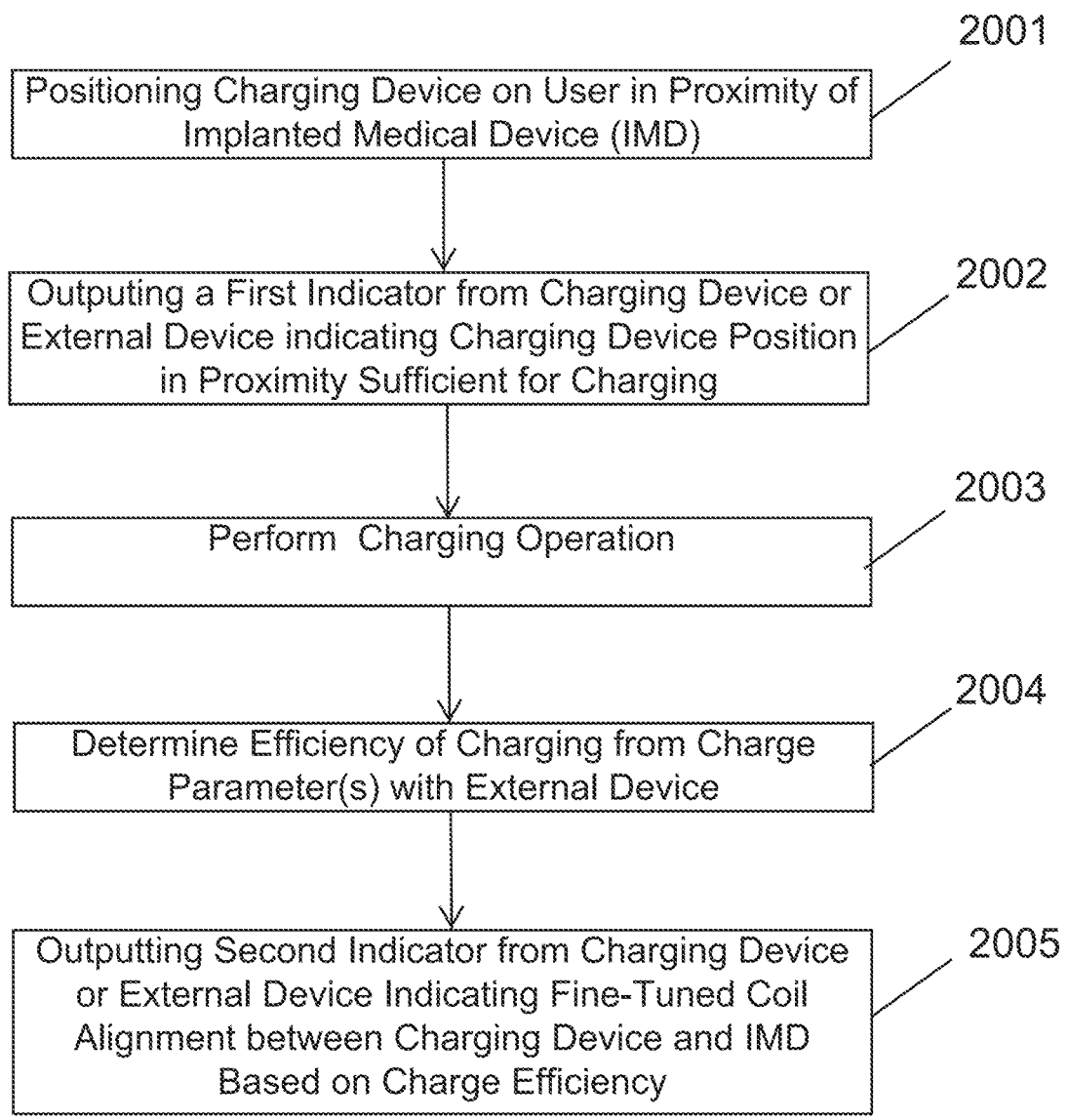

FIG. 19-20 shows exemplary methods of charging an implanted device with a charging device and an alignment indicator, in accordance with some embodiments.

As shown in FIG. 19, the method can include steps of: initiating the fine-tuned charger alignment procedure on an external device 1901; establishing communication between charger device and external device 1902; performing charging operation with the charger device 1903 and communicating one or more charge parameters to the external device; determining charging efficiency from charge parameter(s) with the external device 1904; and outputting, in real-time, an alignment indicator based on the charge efficiency with external device during adjustment of the position of the charging device 1905. It is appreciated that the alignment indicator can include one or more of the features described herein, or in combination (e.g. visual, audio, haptic).

As shown in FIG. 20, such methods can include steps of: positioning a charging device on user in proximity of implanted medical device (IMD) 2001; outputting a first indicator from charging device or external device indicating charging device position in proximity sufficient for charging 2002; performing a charging operation; determining efficiency of charging from charge parameter(s) with external device or charging device 2004; and outputting second indicator from charging device or external device indicating fine-tuned coil alignment between charging device and IMD based on charge efficiency 2005. It is appreciated that the alignment indicator can include one or more of the features described herein, or in combination (e.g. visual, audio, haptic).

In another aspect, functionality of the charging device in regard to any of the alignment indicator features herein can be effected by a software push through an external device in communication with the charging device, for example, the clinician programmer or the patient's personal computing device (e.g. smartphone). In some embodiments, the specialized software configured for fine-tuned alignment can facilitate the software push through the clinician programmer or the patient's personal computing device to the charging device. In some embodiments, the specialized software application can be configure to upgrade the software on the implanted medical device (e.g. IPG) through the charging device from the user device while the charging device is positioned on the patient's body over the IPG (e.g. immediately prior, during or after charging). The upgrade can include features pertaining to charge alignment and/or various other features unrelated to charging alignment. In another aspect, the periodic communication between the user device and the charging device during charging sessions can be utilized for various auxiliary functions, including programming of stimulus profiles from the user device (e.g. by the clinician or sent by the clinician to the patient's user device) and/or downloading data logs from the implanted device.

In the foregoing specification, the invention is described with reference to specific embodiments thereof, but those skilled in the art will recognize that the invention is not limited thereto. As used herein "user device" can refer to a device of any of a patient, a clinician or a clinical specialist associated with the device manufacturer. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A system for facilitating fine-tune alignment between an external charging device and an implantable medical device in a patient, the system comprising:
   an external charging device having a charging coil disposed within a housing and configured to magnetically couple with a corresponding receiving coil of the implantable neurostimulator, wherein the external charger includes an antenna configured for communicating with one or more external devices, and a processor configured to control charging with the charging coil and monitor one or more charging parameters during charging, wherein the external charger comprises one or more indicators that are configured to indicate a first-order alignment of the charging device with the implantable medical device;
   a portable user device of the patient, a clinician or a clinical specialist, the user device having a housing and further including:
   an antennae for communicating with the external charging device and/or the implantable medical device;
   a user interface; and
   a processor operably coupled to the antennae and user interface, the processor being configured to:
      establish communication with the external charging device;
      receive a communication of the one or more charging parameters or an associated metric during charging;
      determine a value corresponding to the charging metric or one or more charging parameters during charging and determine a target range and/or value for a desired second-order, fine-tuned alignment during charging; and
      output an alignment indicator that corresponds to alignment between the external charging device and the implanted medical device via the user interface during charging to indicate the second order, fine-tuned alignment between the external charging device and the implanted medical device by manual adjustment, wherein the indicator is based on the one or more charging parameters or the associated metric.

2. The system of claim 1, wherein the one or more indicators of the charging device comprise an audio alert to indicate that the first-order alignment is suitable for charging.

3. The system of claim 2, wherein the one or more indicators of the charging device further comprise a haptic indicator when the charging device loses inductive coupling indicating first-order alignment is unsuitable for charging to facilitate realignment by patient.

4. The system of claim 1, wherein the user device is configured to determine the associated metric and output the associated metric to the user interface, wherein the associated metric is a charging efficiency.

5. The system of claim 1, wherein the user device further comprises an output of directional guidance in regard to manual positioning of the charging device to achieve the desired second-order alignment.

6. The system of claim 1, wherein the target range and/or value is a function of a plurality of values obtained during the charging session.

7. The system of claim 6, wherein the target range and/or value is a function of a plurality of values obtained during a plurality of charging sessions.

8. The system of claim 6, wherein the target range is less than a total range of values determined during charging.

9. The system of claim 8, wherein the target range is a range of determined charging efficiencies during charging.

10. The system of claim 1, wherein the one or more charge parameters include any of: an output power of the charging device and a received power within the implanted medical device; a voltage of the charging device and corresponding voltage in the implanted medical device; and a current of the charging device and corresponding current induced in the implanted medical device.

11. The system of claim 1, wherein user device is any of: a clinician programming device, a patient remote, and a portable computing device of the patient, or a clinician specialist device.

12. The system of claim 1, wherein indicator of alignment is based on charging efficiency and the indicator is an output only when the charging efficiency is within an optimal range or a maximum within a range of determined charging efficiencies during charging.

13. The system of claim 1, wherein the value is based on the charging efficiency.

14. The system of claim 1, wherein the charging device functionality pertaining to the alignment indicator is embodied within a software update pushed from the user device.

15. A portable charging device for transcutaneous charging of an implantable medical device in a patient, the charging device comprising:
   a housing having an external surface that is configured to at least partially engage a skin surface of the patient and be positioned at least partially over the implantable medical device;
   an antenna disposed within the housing;
   a charging coil disposed within the housing and configured to magnetically couple with a corresponding receiving coil of the implantable neurostimulator,
   a processor configured to:
      establish communication with the implantable medical device;
      determine a first order alignment based on the magnetic coupling;
      one or more indicators configured to indicate a first-order alignment, wherein the one or more indicators include audio and haptic indicators;
      control charging with the charging coil of the charging device to facilitate recharging of the implanted medical device;
      monitor one or more charge parameters during charging;
      establish communication with a user device of a patient, clinician or clinical specialist, the user device having an alignment indicator for second order, fine-tuned alignment; and
      output, to the user device, a communication via the antenna of one or more charging parameters or an associated metric during charging or a metric based on the one or more charging parameters for determination of second-order, fine-tuned alignment of the charging device with the implanted medical device by the user device.

16. The system of claim 15, wherein the audio indicator is configured to indicate that the first order alignment is suitable for charging.

17. The system of claim 16, wherein the haptic indicator is configured to indicate when the charging device loses inductive coupling indicating first order alignment is unsuitable for charging to facilitate realignment by patient.

18. The portable charging device of claim 15, wherein the one or more charge parameters includes any of: a charge parameter of the charging coil and a corresponding charge parameter of the implanted medical device during charging for determination of charging efficiency; a voltage or current; and a charging efficiency.

19. The portable charging device of claim 15, wherein the user device is a clinician programming device or a clinical specialist device and the processor is configured to authenticate the device before authorizing communication therewith.

20. The portable charging device of claim 15, wherein the charging device is further configured to output of directional guidance in regard to manual positioning of the charging device to achieve the desired second-order alignment.

21. The portable charging device of claim 15, wherein the charging device functionality pertaining to the alignment indicator is embodied within a software update pushed from the user device.

22. The portable charging device of claim 15, wherein the charger device includes an alignment module and a charger module.

23. The portable charging device of claim 22, wherein the alignment module is configured to obtain one or more charging parameters during charging from the charging module without modifying the charging operation and communicates the one or more charging parameters to the user device in a secure authenticated communication.

* * * * *